(12) United States Patent
Blum

(10) Patent No.: US 6,506,592 B1
(45) Date of Patent: Jan. 14, 2003

(54) HYPERTHERMOPHILIC ALPHA-GLUCOSIDASE GENE AND ITS USE

(75) Inventor: Paul Blum, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 09/376,343

(22) Filed: Aug. 18, 1999

Related U.S. Application Data

(60) Provisional application No. 60/096,860, filed on Aug. 18, 1998.

(51) Int. Cl.[7] .......................... C07C 3/00; C07G 17/00; C12N 9/00; C12N 9/14
(52) U.S. Cl. ...................... 435/262; 435/183; 435/195; 435/200; 435/204; 435/205; 435/207; 435/208; 435/267; 435/274
(58) Field of Search ............................ 424/94.6, 94.61; 435/4, 18, 14, 95, 100, 105, 183, 207, 208, 200, 220, 195, 204, 205, 262, 267, 274

(56) References Cited

U.S. PATENT DOCUMENTS

| | | | |
|---|---|---|---|
| 4,729,788 A | | 3/1988 | Hutchins et al. |
| 4,997,665 A | | 3/1991 | Grethlein |
| 5,102,992 A | | 4/1992 | Glasser et al. |
| 5,196,069 A | | 3/1993 | Cullingford et al. |
| 5,352,600 A | | 10/1994 | Gelfand et al. |
| 5,374,555 A | | 12/1994 | Pokora et al. |
| 5,434,071 A | * | 7/1995 | Rosenberg et al. |
| 5,474,700 A | | 12/1995 | Griffin et al. |

OTHER PUBLICATIONS

Rolfsmeier M. et al. Molecular characterizationof the alpha–glucosidase gene (malA) from the hyperthermophilic archaeon S.sulfosartoricus. J. Bacteriol., 1998, vol. 180(5):1287–95, Mar. 1998.*

Rolfsmeier M. et al. Purification and characterization of a maltase from the extermely thermophilic crenarchaeote S.sulfosartoricus. J. Bacteriol., 1995, vol. 177(2):482–85, Jan. 1995.*

Moracci M et al. Expression and extensive characterization of a beta–glycosidase from the extreme thermoacidophilic archaeon S.solfataricus in *E.coli:* authenticity of the recombinant enzyme. Enzyme Microb. Technol. (Nov. 1995), vol. 17(11):992–7.*

Pisani et al. Thermostable beta–galactosidase from archaebacterium S.solfatiricus. Purification and properties. (Jan. 1990), Eur. J. Biochem. vol. 187(2):321–8.*

Nucci R et al. Exo–glucosidase activity and substrate specificity of the beta–glycosidase isolated from extreme thermophile S.solfataricus. Biotechnol. Appl. Biochem., Apr., 1993, vol. 17(2):239–50, Mar. 1998.*

Febbraio F. et al. Identification of the active site nucleophile in the thermostable beta–glycosidase from the archaeon S.solfataricus expressed in *E.coli.* (1997), Biochemistry, vol. 36:3068–3075, Mar. 1998.*

Haseltine, C., et al., "Extragenic Pleiotropic Mutations That Repress Glycosyl Hodrolase Expression in the Hyperthermophilic Archaeon *Sulfolobus solfataricus*," Aug., 1999; pp. 1353–1361, *Genetics.*

Haseltine, C., et al., "Coordinate Transcriptional Control in the Hyperthermophilic Archaeon *Sulfolobus solfataricus*," Jul., 1999; pp. 3920–3927, *J. of Bacteriology.*

Rolfsmeier, M., et al., "Molecular Characterization of the α–Glucosidase Gene (malA) from the Hyperthermophilic Archaeon *Sulfolobus solfataricus*," Mar., 1998; pp. 1287–1295, *J. of Bacteriology.*

Rolfsmeier, M., et al., "Purification and Characterization of a Maltase from the Extremely Thermophilic Crenarchaeote *Sulfolobus solfataricus*," Jan., 1995; pp. 482–485, *J. of Bacteriology.*

Czihal, A., et al., "Gene Farming in Plants: Expression of a Heatstable Bacillus Amylase in Transgenic Legume Seeds," 1999; 155:183–189, *J. Plant Physiol.*

Herbers, K., et al., "A Thermostable Xylanase from *Clostridium thermocellum* Expressed at High Levels in the Apoplast of Transgenic Tobacco Has No Detrimental Effects and Is Easily Purified," Jan., 1995; pp. 63–66, *Bio/Technology.*

Pen, J., et al., "Production of Active *Bacillus Licheniformis* Alpha–Amylase in Tobacco and Its Application in Starch Liquefaction," Mar., 1992; pp. 292–296, *Bio/Technology.*

Morgan F J et al. Characetization of thermostable alpha–amylase from *Bacillus licheniformis* NCIB 6346. J. Appl. Bacteriol., 1981, vol. 50:107–114.*

\* cited by examiner

Primary Examiner—Ponnathapu Achutamurthy
Assistant Examiner—Manjunath N. Rao
(74) *Attorney, Agent, or Firm*—Rothwell, Figg, Ernst & Manbeck

(57) ABSTRACT

Recombinant, thermostable alpha-glucosidases from archaeal micro-organisms and isolated DNA encoding for such alpha-glucosidases are provided. The isolated DNA is obtained by use of DNA or antibody probes prepared from the DNA encoding *S. sulfataricus* alpha-glucosidase. Also provided are methods for producing recombinant archaeal thermostable alpha-glucosidase and transformants incorporating thermostable alpha-glucosidase. Autoprocessing of plant tissue through the use of transgenic thermostable glycosyl hydrolases is described.

9 Claims, 18 Drawing Sheets

FIG 2A

```
1201  TTCAGAGATGATAGACTTGTTACCACTTTTCCAGATAACGTAGTTCACTACTTGAGGGGA    1741  GAGAAGGGACATCCGGTAATTAGACCTCTATTTAGGAATTCAGAATGATGACGACAATG
      F  R  D  D  R  L  V  T  T  F  P  D  N  V  V  H  Y  L  R  G             E  K  G  H  P  V  I  R  P  L  F  Y  E  F  Q  D  D  D  D  M

1261  AAGAGGGTTAAACACGAAAAAGTTAGAAATGCTTATCCTTTATATGAGGCCATGGCAACG    1801  TATAGAATAGAAGACGTAGTAGCATTACCTAGAGGTAAGTATTTGCTTTACGCTCCAATTGTAAGT
      K  R  V  K  H  E  K  V  R  N  A  Y  P  L  Y  E  A  M  A  T             Y  R  I  E  D  E  Y  M  V  G  K  Y  L  L  Y  A  P  I  V  S

1321  TTTAAGGGGTTTAGGACAAGCCATGGAATGAAATAATATTATCTTGAGTAGCCGGGTTAT    1861  AAAGAGGAGAGTAGTAGTAACATTACCTAGAGGTAAGTGGTACAATTACTGGAAATGGC
      F  K  G  F  R  T  S  H  R  N  E  I  F  I  L  S  R  A  G  Y             K  E  E  S  R  L  V  T  L  P  R  G  K  W  Y  N  Y  W  N  G

1381  GCCGGAAATACAAAGATACCATTCAACTGGACTGTGATAATACCCCTCATGGGATGAT    1921  GAGAATAATAAACGGTAAGAGTGTCTTAAGTCTACTCATGAGTTGCCAATTACTTGAGA
      A  G  I  Q  R  Y  A  F  I  W  T  G  D  N  T  P  S  W  D  D             E  I  I  N  G  K  S  V  V  K  S  T  H  E  L  P  I  Y  L  R

1441  TTGAAGTTCAACTACAAGTCCTTCGGCCTAATGGTTCGGCGAACTTCGGCCTATCGATTTTCTGGT    1981  GAAGGATCAATAATCCCCGTTGGAGGGTGACGAGTAATAGTTTACGTCGAGACCTCGTTC
      L  K  L  Q  L  V  L  G  L  S  I  S  G  V  P  F  V  G                   E  G  S  I  I  P  L  E  G  D  E  L  I  V  Y  G  E  T  S  F

1501  TGTGATATAGGTGGATTTCAAGGCAGAAACTTCGCGGAAATTGACAATTCTATGGATTTA    2041  AAGCGTTACGATGTAACTAAGCTAACTACATCAGAGAAAACCAGTGACGAAGATAAGTTGAC
      C  D  I  G  G  F  Q  G  R  N  F  A  E  I  D  N  S  M  D  L             K  R  Y  D  M  A  E  I  T  S  S  N  E  I  K  F  S  R  E

1561  TTAGTCAAATATATGCTGGAACCAGTTCCTTAGCCCTGTTCTTCCCCTTCTAGAGGTAACT    2101  ATTTATGTATCTAAGCTAACTACATCAGAGAAAACCAGTGACGAAGATAATAGTTGAC
      L  V  K  Y  Y  A  L  A  L  F  P  P  Y  R  S  H  K  A  T                I  Y  V  S  K  L  I  T  S  S  E  K  P  V  S  K  I  I  V  D

1621  GATGGTATAGATACGGAACCAGTTTTCCTGCCAGATTACTATAAGGAGAAAGTAAGGAA    2161  GATAGTAAGGAAATTCAAGTAGAGAAGACAATGCAAAAACACTTACGTTGCTAAGATTAAT
      D  G  I  D  T  E  P  V  F  L  P  D  Y  Y  K  E  K  V  K  E             D  S  K  E  I  Q  V  E  K  T  M  Q  N  T  Y  V  A  K  I  N

1681  ATCGTGGAGTTGAGGTATATACGGTACAAGTTCTTACCCTATATTATTCCTAAGCTTAGT    2201  CAAAAAATTAGGGAAAGATTAACCTAGAGTAGTTTTTCACGTACTCCAAGGACTTAAC
      I  V  E  L  R  R  Y  K  F  L  P  Y  I  Y  S  L  A  L  E  A  S          Q  K  I  R  G  K  I  N  L  E  *
```

FIG 2B pH optima for maltose and glycogen hydrolysis. Maltose hydrolysis. Buffers were as follows: pH 2.0 to 5.0, 100 mM sodium acetate (closed circles); pH 3.5 to 9.0, 100 mM sodium phosphate (open circles).

pH optima for maltose and glycogen hydrolysis. Glycogen hydrolysis. Buffers were as follows: pH 2.0 to 5.0, 100 mM sodium acetate (closed circles); pH 3.5 to 9.0, 100 mM sodium phosphate (open circles).

HYPERTHERMOPHILIC ALPHA-GLUCOSIDASE GENE AND ITS USE

This application is related to U.S. provisional patent application Ser. No. 60/096,860, filed Aug. 18, 1998, incorporated herein by reference.

BACKGROUND OF THE INVENTION

The present invention relates to a novel nucleic acid coding for a thermostable glycosyl hydrolase, alpha-glucosidase, from the archaeon *Sulfolobus solfataricus* and a novel enzyme coded by its gene, malA. It also relates to bacteria and plants transformed with hyperthermophilic alpha-glucosidase and a method for preparing the recombinant alpha-glucosidase by use of the same. The present invention further relates to a method of using the transgenic thermostable glycosyl hydrolases for the bioprocessing of plant carbohydrates.

The publications and other materials used herein to illuminate the background of the invention or provide additional details respecting the practice, are incorporated by reference, and for convenience are, in part, respectively grouped in the appended List of References.

A variety of industries, such as food and chemical, employ hydrolases for the production of glucose, sucrose and other sugars. High value is placed on thermostability and thermoactivity of enzymes for use in the bioprocessing of starch into maltodextrins, glucose, fructose and various other sugars.

One hydrolase, alpha-glucosidase, is defined by the International Union of Biochemistry as an enzyme which hydrolyzes glucose oligomers to glucose. Alpha-glucosidase and other glycosidase genes from non-thermophilic eukaryotic and eubacterial organisms have been cloned and characterized (Hermans, et al., 1991). In addition, the major, endogenous, soluble alpha-glucosidase from *Sulfolobus solfataricus* has been purified and characterized. Although it has not, to date, been cloned, the native enzyme hydrolyzes sucrose and liberates glucose from maltose. It has a temperature optimum in excess of 100° C., with a prolonged half life at elevated temperatures, and is resistant to proteolysis and denaturants including chaotropes, detergents and aliphatic alcohols (Rolfsmeier and Blum, 1995). Another hydrolase from *S. solfataricus*, beta-glycosidase, has been characterized (Haseltine, et al., 1999(a)).

Plant-derived polysaccharides are used in enormous quantities as foods (sugar) and, following conversion, in other specialty and value added chemicals such as ethanol. Consequently, these materials are recognized as essential and are traded as commodities. Indeed, key measures of inflation are strongly influenced by the value assigned to such commodities. Sugar (glucose) is produced by bioprocessing of plant starch from plants including corn, sugar beets and sugar cane. Incremental improvements in sugar production reflect two basic strategies, increasing the yield of polysaccharide on a per plant mass basis and increasing the conversion of endogenous starch into sugar. Where the former approach results from advances in plant breeding, the latter approach initiated the introduction of microbial gene products as cell-free bioprocessing components. Key among these additives are two enzymes, alpha-amylase and glucoamylase, which are employed as commodity materials. Alpha-amylase is an endo-acting enzyme which debranches starch yielding dextrin. Glucoamylase is an exo-acting enzyme which serially hydrolyzes dextrin subunits into free glucose. Plant starch hydrolysis requires hydration to enable enzyme action, consequently the introduction of water is a critical first step and is conventionally performed by heating and extrusion. Cost effective bioprocessing necessitates rapid throughput therefore, a thermostable alpha-amylase is commonly added to enable immediate debranching of hydrated starch. However, both the pH and the temperature of the bioprocessing reactors must thereafter be adjusted to create near-neutral and reduced temperatures to support activity of the commercial glucoamylase. As a result, a source of transgenic, thermostable glycosyl hydrolases would be an important contribution to the starch processing industry due to their activity at high temperatures and extreme stability at room temperatures, which offers extended shelf life. Although glycosyl hydrolases occur among the hyperthermophillic archaea (Costantino, et al., 1990; Rolfsmeir and Blum, 1995; Haseltine, et al., 1999(a)), their culture as a source of enzyme is complicated by their extreme growth requirements. Furthermore, expression of archaeal enzymes in heterologous hosts is complicated by the altered environment in which expression occurs and difficulty with translation and post translational processing (Trent, et al., 1991). Over production of archaeal proteins in plants would require that the protein fold properly in plants which, for thermostable proteins, may require chaperones not normally present in plants. To date, no archaeal alpha-glucosidase genes have been cloned or expressed recombinantly.

SUMMARY OF THE INVENTION

The present invention relates to a novel nucleic acid coding for a thermostable glycosyl hydrolase, alpha-glucosidase, from the archaeon *Sulfolobus solfatoricus* and a novel enzyme coded by its gene, malA. It also relates to bacteria and plants transformed with hyperthermophilic alpha-glucosidase and a method for preparing the recombinant alpha-glucosidase by use of the same. The present invention further relates to a method of using the transgenic thermostable glycosyl hydrolases for the bioprocessing of plant carbohydrates.

The malA gene of the present invention has been identified, cloned and expressed in bacteria and plants. The distribution and associated activity of the malA gene in the three most common members of the Sulfolobus genus have been determined.

The purified alpha-glucosidase produced by the recombinant malA gene, provides an extremely thermostable enzyme which is able to hydrolyze a surprisingly wide range of polysaccharides to glucose. Substrates include starch and maltodextrins indicating that the enzyme acts as both an alpha-amylase and an alpha-glucosidase. Additionally, sucrose is hydrolyzed to invert sugar by the malA gene product, indicating the enzyme is also a sucrase.

Extracts of transgenic plants of the present invention expressing thermostable glycosyl hydrolases have been prepared. The plant extracts are able to undergo "autohydrolysis" of plant polysaccharide into glucose and other sugars. The recombinant glycosyl hydrolases expressed in the transgenic plants are nontoxic in plant tissues because the enzymes are inactive at temperatures supporting plant growth and therefore do not significantly interfere with normal metabolism in the living plant. Thus, regulated plant promoters are not required and constitutive promoters are sufficient. When desired, the transgenic plant tissue can be heated to activate the enzymes, causing in situ processing of storage carbohydrates to glucose and other small molecules by the recombinant plant extract, itself. This obviates the need to add separately produced commodity enzymes to plant material, as is the current method used in industry.

Accordingly, this invention comprises the following aspects:

1) An isolated nucleic acid molecule encoding thermostable alpha-glucosidase comprising the nucleotide sequence of SEQ ID NO:1.
2) An expression vector comprising the nucleotide sequence of SEQ ID NO: 1.
3) Transformed host cells comprising the nucleotide sequence of SEQ ID NO: 1.
4) Transformed host cells expressing the recombinant amino acid sequence of SEQ ID NO:2.
5) Methods of preparing the transformed hosts of 4).
6) Methods for extracting and purifying heterologous, thermostable glycosyl hydrolases from transformed host cells.
7) Characterization of recombinant glycosyl hydrolase enzymes, including their useful chemical and physical properties and utility for industrial applications.
8) Novel recombinant enzyme of 7) comprising the amino acid sequence of SEQ ID NO:2.
9) Transgenic plant cells expressing thermostable glycosyl hydrolases that are capable of autohydrolysis (in situ processing) of substrate into glucose and other small molecules.

BRIEF DESCRIPTION OF THE DRAWINGS

FIGS. 2A and 2B show the DNA sequence (SEQ ID NO:1) and deduced, encoded amino acid sequence (SEQ ID NO:2) of the malA gene.

FIG. 5A shows levels of alpha-glucosidase activity in independent transformed plants. FIG. 5B shows levels of beta-glycosidase activity in independent transformed plants.

FIG. 7A. Glucose released by the alpha-glucosidase using an exogenous starch as substrate. A 5% (w/v) solution of soluble starch was incubated at 80° C. with no additions (closed circles), with a protein extract from a plant transformed with an empty vector (open circles) and with a protein extract from transformant MI52E containing the alpha-glucosidase (closed squares).

FIG. 11A shows levels of alpha-glucosidase. Mean enzyme specific activities representing samples from five leaves (closed circles) were determined from the same plant at the indicated times after plant seeding. Total leaf protein (open circles) was determined per leaf area. FIG. 11B shows levels of beta-glycosidase.

FIG. 12A shows a colormetric western blot analysis of alpha-glucosidase in transgenic plant leaves. Lane 1, *E. coli*-derived recombinant alpha-glucosidase; lane 2, protein extract of transformant MI52E; lane 3, protein extract of plant transformed with an empty vector. Samples for western blots were loaded in 20 µg amounts per lane. Blots were probed with rabbit anti-beta-glycosidase polyclonal antibodies. FIG. 12B shows a colormetric western blot analysis of beta-glycosidase in plant leaves. Lane 1, protein extract of transformant JJ-6; lane 2, protein extract of plant transformed with an empty vector; lane 3, extract of *E. coli* containing pUC19; lane 4, *E. coli*-derived recombinant beta-glycosidase. FIG. 12C. Immunoprecipitation of alpha-glucosidase activity from transformant MI52E.

SUMMARY OF SEQUENCE LISTING

Figure 1A:
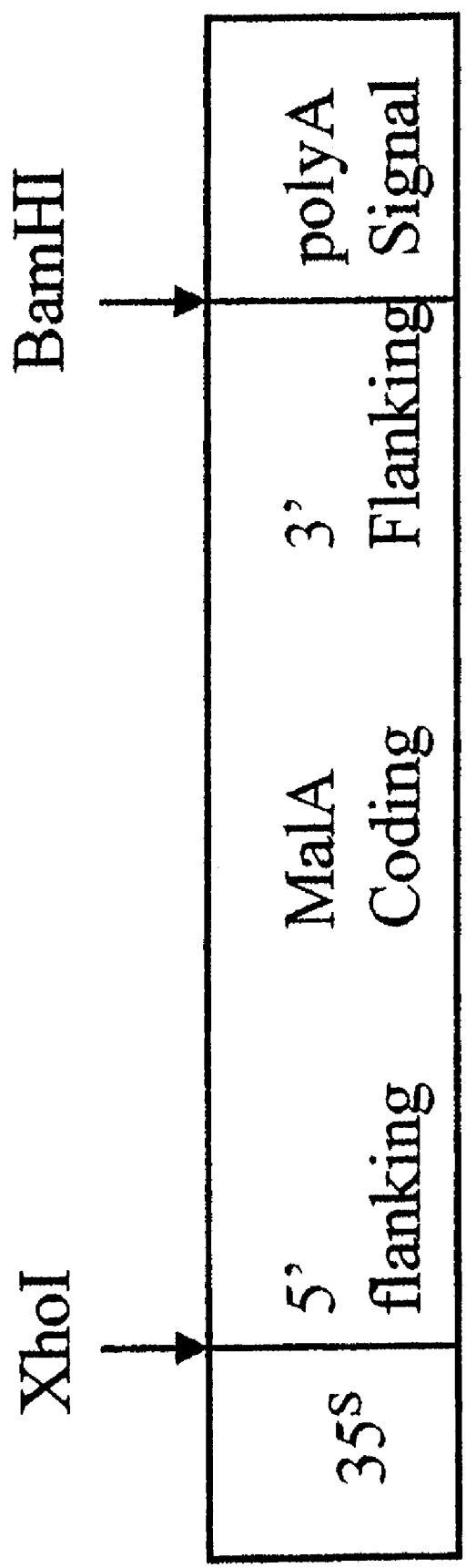
FIGS. 1A and 1B are the malA coding region and a gene construct containing the malA gene from *Sulfolobus solfataricus*. The malA coding sequence plus 30 bp of the malA promoter region was cloned into the Xho I/Bam HI site of the plant expression vector pRTL2 between the enhanced 35S promoter and the 35S polyadenylation signal. The 3.5 kb Pst I fragment of the resulting plasmid was then cloned into the multiple cloning site of the binary vector pPZP112 to produce the construct pPB709 for transformation into plants.

SEQ ID NO:1 is the nucleotide sequence for the malA gene. SEQ ID NO:2 is the amino acid sequence for the malA protein. SEQ ID NO:3 is the N-terminal amino acid sequence for alpha-glucosidase from *S. sulfataricus*. SEQ ID NO:4 is the amino acid sequence for alpha-glucosidase generated by chemical cleavage with cyanogen bromide.

DETAILED DESCRIPTION OF THE INVENTION

The present invention relates to a novel nucleic acid coding for a thermostable glycosyl hydrolase, alpha-glucosidase, from the archaeon *Sulfolobus solfatoricus* and a novel enzyme coded by its gene, malA. It also relates to bacteria and plants transformed with hyperthermophilic alpha-glucosidase and a method for preparing the recombinant alpha-glucosidase by use of the same. The present invention further relates to a method of using the transgenic thermostable glycosyl hydrolases for the bioprocessing of plant carbohydrates.

Cloning, Characterization and Expression of malA Gene

Figure 2A:
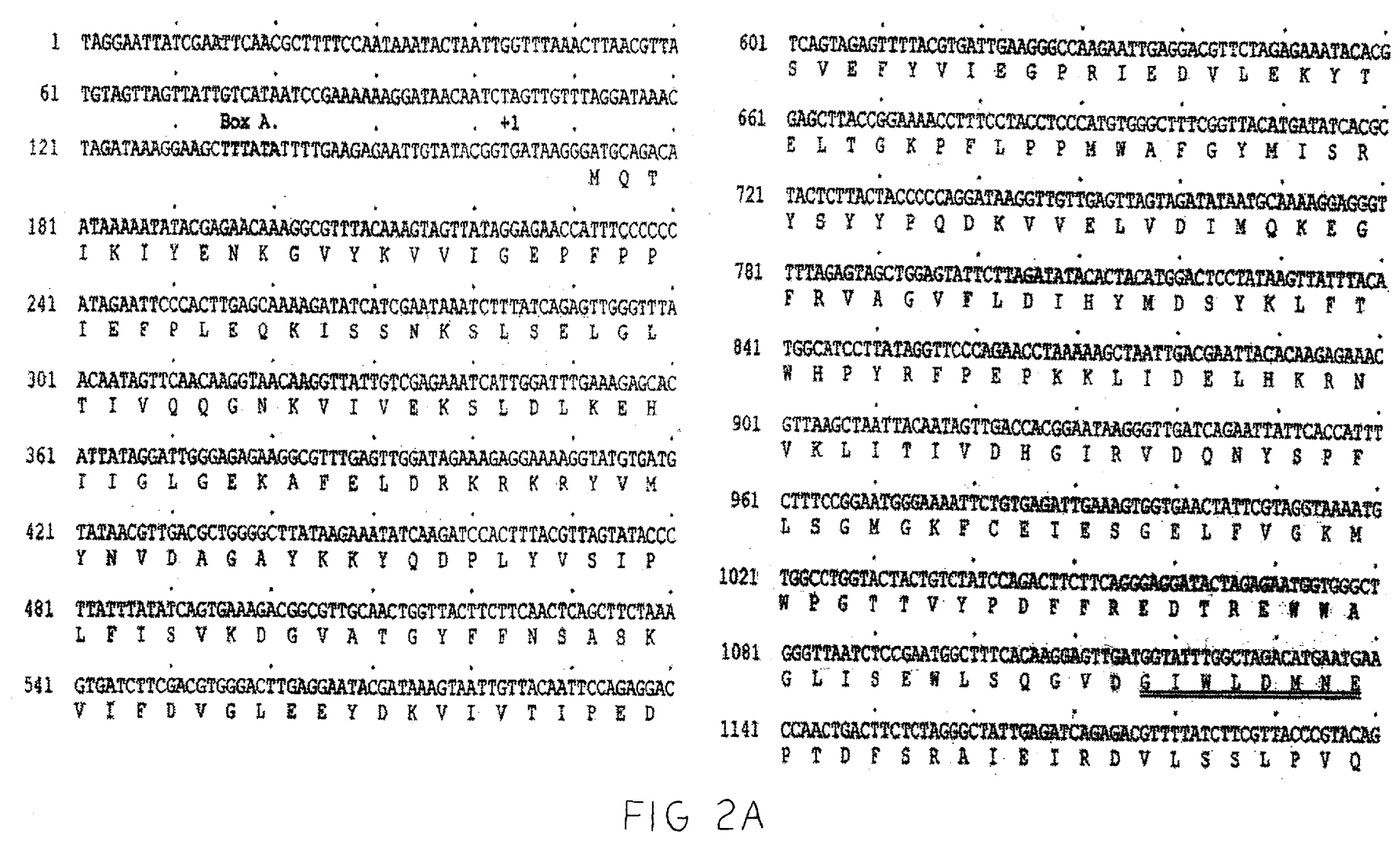

Using gene-specific PCR primers derived from the alpha-glucosidase protein sequence as probe to screen a genomic *S. solfataricus* 98/2 phage lambda library, the malA gene of the present invention has been cloned and characterized (GenBank Accession No. AF042494). The nucleotide sequence is set forth as SEQ ID NO:1 (FIG. 2), and the amino acid sequence is set forth as SEQ ID NO:2 (FIG. 2). It has been found that the malA sequence comprises 2,083 bp encoding a protein of 693 amino acids.

In carrying out this invention, isolation and purification of DNA carrying the genetic information of the thermostable glycosyl hydrolases from *Sulfolobus solfataricus* was performed by conventional means. For instance, restriction digestion and ligation of DNA and DNA sequence analysis were performed as described previously. (Blum, et al., 1992; Rockabrand and Blum, 1995; Haseltine, et al., (1999(a)).

Insertion of chromosomal DNA into vector DNA was performed by digesting the chromosomal DNA and plasmid DNA with restriction enzymes to yield chromosomal DNA and plasmid DNA fragments and treating the mixture of those with DNA ligases.

The resulting plasmids were introduced into a bacterial host and/or used to transform *Agrobacterium tumefaciens* by freeze-thaw method (An, et al., 1988). The transformed *A. tumefaciens* was used to transform plants by the leaf disc method of Horsch, et al., 1985. All manipulations of *Escherichia coli* were as described previously in Rockabrand, et al., 1995.

The production of the recombinant enzymes of this invention were conducted by over expression in *E. coli*. Assays for alpha-glucosidase activity were performed with para-nitrophenyl-alpha-D-glucopyranoside or methylumbelliferyl-alpha-D-glucoside. Assays for hydrolysis of substrate and detection of glucose were monitored by means known in the art. Purification of the recombinant enzyme to apparent homogeneity employed heat fractionation of clarified cell sonicates followed by anion-exchange fast protein liquid chromatography and gel filtration fast protein liquid chromatography as described in Rolfsmeier, et al.,1995.

Autodigestion of Plant Tissue Using Hyperthermophilic Glycosyl Hydrolases

New strategies to accomplish improved plant bioprocessing rest on the merging technology of plant metabolic engineering (Sommerville and Sommerville, 1999). Metabolic engineering of plant biochemistry includes an expanding list of secondary metabolites and modified pathway end products ranging from lipids to small molecules. Balanced against this goal are the physiological consequences resulting from the accumulation of foreign, and possibly toxic, compounds. Clearly improvements in bioprocessing will lead to further improvements in agricultural process economics and create new opportunities to increase the types and amounts of derivative materials. One approach for improving bioprocessing is to eliminate the need to add commodity enzymes for starch hydrolysis. To fit the current technology, however, this necessitates the use of thermotolerant catalysts. In addition, other plant polysaccharides such as beta-linked polymeric sugars are not currently used in commercial processes.

Archaea have recently been recognized as a distinct branch of prokaryotes; as distantly related to bacteria as they are to eukaryotic organisms. (Woese, et al., 1990; Whitman, et al., 1999). They include three dominant biotypes; the hyperthermophiles, the methanogens and the halophiles; each is associated with distinct and extreme environments. The present invention relates to the hyperthermophiles which produce numerous proteins of industrial interest (Cowan, 1992). Key among these activities are those which promote the hydrolysis of plant polysaccharides (Sunna, 1997). Several representative activities from the hyperthermophile *Sulfolbous solfataricus*, are characterized herein at both the genetic and functional level. *S. solfataricus* secretes an acid-resistant thermotolerant alpha-amylase (amyA) which retains full function after one week of 80° C. at pH 3 (Haseltine, et al., 1996; Haseltine, et al., 1999(a)). Two other activities have been characterized: a) a cell associated alpha-glucosidase or alpha-glucosidase (malA) with a temperature optimum of 105° C. which converts dextrins and other alpha-linked polymers into glucose (Rolfsmeier and Blum, 1995), and b) a beta-glycosidase (lacs) which converts beta-linked disaccharides into glucose (Haseltine, et al., 1999(b)). Both the alpha-glucosidase and the beta-glycosidase have been surprisingly discovered to have broad substrate preferences. It has been unexpectedly determined the transgenic plants expressing these last two activities are able, upon heating at elevated temperatures, to undergo a process of autodigestion converting polysaccharides into monosaccharides in a single step.

Definitions

The present invention employs the following definitions.

As used herein, "autodigestion" and "autohydrolysis" is the ability of transgenic plant tissue which encodes for and expresses heterologous thermostable glycosyl hydrolase to undergo hydrolysis of substrate into glucose and other small molecules when subjected to heat.

As used herein, "alpha-glycosidase" refers to an enzyme which splits polysaccharides, through the hydrolysis of glycosidic bonds.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

As used herein, "expression system" refers to DNA sequences containing a desired coding sequence and control sequences in operable linkage, so that hosts transformed with these sequences are capable of producing the encoded proteins. In order to effect transformation, the expression system may be included on a vector, however, the expression system may then also be integrated into the host chromosome.

As used herein, "gene" refers to a DNA sequence that encodes a recoverable bioactive polypeptide or precursor. The polypeptide can be encoded by a full-length gene sequence or any portion of the coding sequence so long as the enzyme activity is maintained.

As used herein, "glycosyl hydrolase" refers to enzymes which hydrolyze substances linked by glycosyl bonds, for example, polysaccharides.

As used herein, "hyperthermophilic" refers to an organism capable of growth above 70 degrees C., or proteins derived from such an organism.

"Isolated" or "substantially pure". An "isolated" or "substantially pure" nucleic acid (e.g., an RNA, DNA or a mixed polymer) or protein is one which is substantially separated from other cellular components which naturally accompany a native sequence or protein, e.g., ribosomes, polymerases, many other sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"malA Allele" refers to normal alleles of the malA gene.

"malA Locus", "malA Gene", "malA Nucleic Acids" or "malA Polynucleotide" each refer to polynucleotides, all of which are in the malA region, that are likely to be expressed in normal tissue. The malA locus is intended to include coding sequences, intervening sequences and regulatory elements controlling transcription and/or translation. The malA locus is intended to include all allelic variations of the DNA sequence.

These terms, when applied to a nucleic acid, refer to a nucleic acid which encodes an archaeal malA polypeptide, fragment, homolog or variant, including, e.g., protein fusions or deletions. The nucleic acids of the present invention will possess a sequence which is either derived from, or substantially similar to a natural malA-encoding gene or one having substantial homology with a natural malA-encoding gene or a portion thereof.

The malA gene or nucleic acid includes normal alleles of the malA gene, including silent alleles having no effect on the amino acid sequence of the malA polypeptide as well as alleles leading to amino acid sequence variants of the malA polypeptide that do not substantially affect its function. These terms also include alleles having one or more mutations which adversely affect the function of the malA polypeptide. A mutation may be a change in the malA nucleic acid sequence which produces a deleterious change in the amino acid sequence of the malA polypeptide, resulting in partial or complete loss of malA function, or may be a change in the nucleic acid sequence which results in the loss of effective malA expression or the production of aberrant forms of the malA polypeptide.

The malA nucleic acid may be that shown in SEQ ID NO:1 or it may be an allele as described above or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus nucleic acids according to the present invention may include a sequence different from the sequence shown in SEQ ID NO:1 yet encode a polypeptide with.the same amino acid sequence as shown in SEQ ID NO:2. That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NO:2. Nucleic acid encoding a polypeptide which is an amino acid sequence variant, derivative or allele of the amino acid sequence shown in SEQ ID NO:2 is also provided by the present invention.

The malA gene also refers to (a) any DNA sequence that (i) hybridizes to the complement of the DNA sequences that encode the amino acid sequence set forth in SEQ ID NO:2 under highly stringent conditions (Ausubel, et al., 1992) and (ii) encodes a gene product functionally equivalent to malA, or (b) any DNA sequence that (i) hybridizes to the complement of the DNA sequences that encode the amino acid sequence set forth in SEQ ID NO:2 under less stringent conditions, such as moderately stringent conditions (Ausubel, et al., 1992) and (ii) encodes a gene product functionally equivalent to malA. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the malA region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. This number of nucleotides is usually about the minimal length required for a successful probe that would hybridize specifically with an malA-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook, et al., 1989 or Ausubel, et al., 1992. Reagents useful in applying such techniques, such as restriction enzymes and the like, are widely known in the art and commercially available from such vendors as New England BioLabs, Boehringer Mannheim, Amersham, Promega, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, "operably linked" refers to a juxtaposition wherein the components so described are in a relationship permitting them to function in their intended manner. For example, a promoter is linked to a coding sequence if the promoter affects its transcription or expression.

As used herein, a "portion" of the malA locus or region or allele is defined as having a minimal size of at least about eight nucleotides, or preferably about 15 nucleotides, or more preferably at least about 21 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides, or any number of nucleotides between 500 and the number shown in SEQ ID NO:1. The present invention includes all novel nucleic acids having at least 8 nucleotides derived from SEQ ID NO:1, its complement or functionally equivalent nucleic acid sequences. The present invention does not include nucleic acids which exist in the prior art. That is, the present invention includes all nucleic acids having at least 8 nucleotides derived from SEQ ID NO:1 with the proviso that it does not include nucleic acids existing in the prior art.

"malA protein" or "malA polypeptide" refers to a protein or polypeptide encoded by the malA locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native malA sequence, preferably in excess of about 90%, and more preferably at least about 95% homologous. Also included are proteins encoded by DNA which hybridizes under high or low stringency conditions, to malA-encoding nucleic acids and closely related polypeptides or proteins retrieved by antisera to the malA protein(s).

The malA polypeptide may be that shown in SEQ ID NO:2 which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the malA polypeptide. Such polypeptides may have an amino acid sequence which differs from that set forth in SEQ ID NO:2 by one or more of addition, substitution, deletion or insertion of one or more amino acids, provided such polypeptides have malA function.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the malA polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acid side chains may be considered. The importance of the hydropathic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Probes". Polynucleotide sequences associated with malA or lacS alleles are detected by hybridization with a polynucleotide probe which forms a stable hybrid with that of the target sequence, under highly stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of an malA or lacS susceptibility allele.

Probes for malA or lacS alleles may be derived from the sequences of the respective region, its cDNA, functionally equivalent sequences, or the complements thereof. The probes may be of any suitable length, which span all or a portion of the respective region, and which allow specific hybridization to the region. If the target sequence contains a sequence identical to that of the probe, the probes may be short, e.g., in the range of about 8–30 base pairs, since the hybrid will be relatively stable under even highly stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding malA are preferred as probes. This definition therefore includes probes of sizes 8 nucleotides through 9000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides, or any number of nucleotides between 500 and the number of nucleotides in SEQ ID NO:1. The probes may also be used to determine whether mRNA encoding malA is present in a cell or tissue. The present invention includes all novel probes having at least 8 nucleotides derived from SEQ ID NO:1, its complement or functionally equivalent nucleic acid sequences. The present invention does not include probes which exist in the prior art. That is, the present invention includes all probes having at least 8 nucleotides derived from SEQ ID NO:1 with the proviso that they do not include probes existing in the prior art.

Similar considerations and nucleotide lengths are also applicable to primers which may be used for the amplification of all or part of the malA gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether mRNA encoding malA is present in a cell or tissue. The present invention includes all novel primers having at least 8 nucleotides derived from the malA locus for amplifying the malA gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for malA polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $P^{35}$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, enzymatic activity and other biological activities characteristic of malA polypeptides.

The present invention also provides for fusion polypeptides, comprising malA polypeptides and fragments. Homologous polypeptides may be fusions between two or more malA polypeptide sequences or between the sequences of malA and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides are described, for example, in Merrifield, 1963.

"Protein purification", unless otherwise specifically described or incorporated herein, refers to various methods for the isolation of the malA and lacS polypeptides from other biological material, such as from cells transformed with recombinant nucleic acids encoding malA or lacS, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% w/w of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

malA and lacS proteins are substantially free of naturally associated components when they are separated from the native contaminants which accompany them in their natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide", as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

To determine homology between two different nucleic acids, the percent homology is to be determined using the BLASTN program "BLAST 2 sequences". This program is available for public use from the National Center for Biotechnology Information (NCBI) over the Internet (http://www.ncbi.nlm.nih.gov/gorf/bl2.html) (Altschul et al., 1997). The parameters to be used are whatever combination of the following yields the highest calculated percent homology (as calculated below) with the default parameters shown in parentheses:

Program—blastn
Matrix—0 BLOSUM62
Reward for a match—0 or 1 (1)
Penalty for a mismatch—0, −1, −2 or −3 (−2)
Open gap penalty—0, 1, 2, 3, 4 or 5 (5)
Extension gap penalty—0 or 1 (1)
Gap x_dropoff—0 or 50 (50)
Expect—10

Along with a variety of other results, this program shows a percent identity across the complete strands or across regions of the two nucleic acids being matched. The program shows as part of the results an alignment and identity of the two strands being compared. If the strands are of equal length then the identity will be calculated across the complete length of the nucleic acids. If the strands are of unequal lengths, then the length of the shorter nucleic acid is to be used. If the nucleic acids are quite similar across a portion of their sequences but different across the rest of their sequences, the blastn program "BLAST 2 Sequences" will show an identity across only the similar portions, and these portions are reported individually. For purposes of determining homology herein, the percent homology refers to the shorter of the two sequences being compared. If any one region is shown in different alignments with differing percent identities, the alignments which yield the greatest homology are to be used.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type malA or lacs nucleic acid or wild-type malA or lacS polypeptide. The modified polypeptide will be substantially homologous to the wild-type polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type polypeptide. Alternatively, the similarity of function (activity) of the modified polypeptide may be higher than the activity of the wild-type polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type gene function produces the modified protein described above.

As used herein, "thermostable" when referring to an enzyme means an enzyme which can function at high temperatures and is stable to heat, heat resistant, and will not denature at high temperatures.

A polypeptide "fragment", "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991.

Preparation of Recombinant or Chemically Synthesized Nucleic Acids: Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured plant, mammalian or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage and Caruthers, 1981, or the triester method according to Matteucci and Caruthers, 1981, and may be performed on commercial, automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcription terminator sequences, and mRNA stabilizing sequences. Such vectors may be prepared by means of standard recombinant techniques well known in the art and discussed, for example, in Sambrook et al., 1989 or Ausubel et al., 1992.

An appropriate promoter and other necessary vector sequences will be selected so as to be functional in the host, and may include, when appropriate, those naturally associated with the malA gene. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, Cold Spring Harbor, N.Y. (1983). See also, e.g., U.S. Pat. Nos. 5,691,198; 5,735,500; 5,747,469 and 5,436,146.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see Kubo, et al., 1988), or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the malA nucleic acid or portions thereof in vectors or other expression vehicles in compatible prokaryotic or eukaryotic host cells. The most commonly used prokaryotic hosts are strains of *Escherichia coli,* although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.), 1979. Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. Production of a particular product based on temperature sensitivity may serve as an appropriate marker. In prokaryotic hosts, the transformant may be selected, e.g., by resistance to ampicillin, tetracycline or other antibiotics.

Prokaryotic or eukaryotic cells transformed with the polynucleotides of the present invention will be useful not only for the production of the nucleic acids and polypeptides of the present invention, but also, for example, in studying the characteristics of malA polypeptide.

The probes and primers based on the malA gene sequence disclosed herein are used to identify homologous malA gene sequences and proteins in other species. These gene sequences and proteins are used in the methods described herein.

Method of Use: Bioprocessing of Plant Carbohydrates

Bioprocessing of plant carbohydrates such as starch currently necessitates commodity enzyme additives to accelerate polysaccharide hydrolysis. Depolymerization is accomplished by heat-based hydration followed by the addition of microbial-derived thermostable hydrolases. To simplify the current process, transgenic tobacco plants of the invention were created which expressed hyperthermophilic glycosyl hydrolase derived from the archaeon *Sulfolobus solfataricus.* Hydrolysis, by recombinant glycosyl hydrolase, of endogenous starch present in starch-containing plant tissues such as corn, wheat, milo and the like, was accomplished by processing milled tissue, at high temperatures to activate the recombinant protein. Alternatively, plant starch was first separated from other components of the plant tissue and then hydrolyzed by addition of recombinantly produced glycosyl hydrolase and subjecting the mixture to high temperatures. Conventionally, in the wet milling process there is separation of the germ, hull gluten. In order to separate starch from the corn kernel, for example, the kernels are steeped in an aqueous solution under controlled conditions to soften the kernels and facilitate separation of the kernels' components. After steeping, the aqueous solution is ground and screened so as to separate the fibrous material and endosperm particles from the soluble protein, starch and gluten. The starch and gluten are then separated by their differences in density, for example, by high-rate washing centrifugation. Alternatively, other methods may be employed in the isolation of starch from starch-containing plant tissue such as addition of cellulose at the milling step or separation of starch from oil-bearing solids by centrifugation to promote an oil-solid phase separation.

Enzyme substrates included exogenous polysaccharides of defined composition and plant extracts enriched for endogenous polysaccharides. Direct conversion of plant tissue into free sugar was demonstrated by the production of high cell density microbial cultures resulting from using heated plant extracts as growth media.

EXAMPLES

The following examples are provided to further illustrate the present invention and are not intended to limit the invention beyond the limitations set forth in the appended claims.

Example 1

Cloning and Characterization of the *Sulfolobus solfataricus* malA Gene

Archaea constitute a third domain of organisms along with eubacteria and eukaryotes. The Archaea was first recognized in the early 1970s and includes single-celled organisms that are found in extreme environments such as volcanic hot springs and hypothermal vents in the deep ocean. Members of the domain include the Methanogen, Halophile and Sulfolobus genera. Members of the genus Sulfolobus have been assigned to the crenarchaeotal subdivision of the domain Archaea, of which Sulfolobus comprises the largest genus. (Burggraf, et al., 1997). *S. solfataricus* is an aerobic, extremely thermophilic organism found in acidic hot springs. The ability of thermophiles, including members of the Sulfolobus genus to grow on a variety of sugars and polysaccharides, is a result of their synthesis of alpha-glucosidases and beta-glycosidases. To investigate poly-saccharide utilization of maltose by Sulfolobus species, the gene encoding the alpha-glucosidase from *S. solfataricus* was cloned and characterized.

Cloning of the gene was accomplished by using gene-specific PCR primers derived from the *S. solfataricus* alpha-glucosidase protein sequence Rolfsmeir et al., 1998. Amino acid sequencing indicated the mature N-terminal alpha-glucosidase sequence was MQTIKIYENLGVYLWIGEP (SEQ.ID.NO:3). Since the purified *S. solfataricus* alpha-glucosidase is generally resistant to proteolytic degradation (Rolfsmeir and Blum, 1995) protein fragments for internal N-terminal sequence analysis were generated by chemical cleavage with cyanogen bromide. A fragment of 19 kDa was selected and yielded the N-terminal sequence VGKYL-LYAPI (SEQ.ID.NO:4). The resulting amino acid sequence information was used to design degenerate oligonucleotides which were then used to amplify a DNA fragment of 1.6 kb by PCR. A 731-bp HindIII-EcoRV fragment derived from the resulting 1.6-kb PCR product was used to generate a radio labeled probe for Southern hybridization to verify the origin of the amplification product. This probe cross-hybridized with single DNA fragments of 1.2, 1.7, and 1.4 kb in HindIII, XbaI, and HincII genomic digests, respectively, of S. solfataricus DNA. The probe was used to screen a genomic S. solfataricus phage λ library consisting of 672 individually propagated recombinant phages by Southern blot analysis. A single isolate was identified (λ7F7), which contained a 15.1-kb insert of S. solfataricus DNA. Southern blot analysis of restriction digests of the λ7F7 phage was performed with the PCR-derived probe. Cross-hybridizing restriction fragments which were identical in size to those observed previously with genomic DNA were observed and indicated that the coding region for alpha-glucosidase is contained in a 4.3-kb BamHI fragment of the λ7F7 insert. This 4.3-kb BamHI fragment was subcloned and sequenced. The sequence located immediately 5' to the malA coding region was subcloned from λ7F7 as a 2.3-kb SacI-HindIII fragment. A 344-bp SacI-BamHI fragment from the extreme 5' end of this fragment was used as a Southern blot probe to identify the next upstream overlapping λ clone from the genomic S. solfataricus 98/2 library. This isolate was named λ-1H4. A 4.1-kb HindIII-SacI fragment which cross-hybridized to the same SacI-BamHI 344-bp fragment was subcloned from λ-1H4. A 2-kb segment of this 4.1-kb HindIII-SacI fragment was sequenced to complete the analysis of putative genes lying 5' to malA. Analysis of regions lying 3' to the malA coding region was done with a 1.8-kb 3' overlapping HindIII-HindIII fragment derived from λ7F7. The resulting sequence comprising a nearly 7-kb DNA contig. has been deposited in Gen Bank (accession number AF042494, incorporated herein by reference).

The alpha-glucosidase open reading frame (ORF) (malA) of the present invention was.identified by comparison of peptide sequences derived from the N-terminal and internal N-terminal sequencing of the natural protein to the deduced amino acid sequence (SEQ ID NO:2). The malA sequence comprises 2,083 bp encoding a protein of 693 amino acids with a predicted mass of 80.5 kDa. This closely corresponds to the apparent mass of the previously purified natural enzyme subunit (Rolfsmeier, et al., 1995). Sequence analysis of the deduced malA product identified a glycosyl hydrolase motif at residues 316 to 323 and an ATP/GTP binding site motif (P loop) at residues 583 to 590 (SEQ ID NO: 2). The glycosyl hydrolase motif contains the putative active-site asparagine previously identified for the human alpha-glucosidase gene (Hermans, et al., 1991). Only two cysteine residues are evident, consistent with the low cysteine content seen previously in thermophilic proteins. There are 14 methionine residues, and the predicted mass of the largest sequence uninterrupted by methionines is 19 kDa as suggested by the-cyanogen bromide cleavage pattern of the alpha-glucosidase. Examination of the 7.05 kb contig identified several ORFs (FIG. 1A) with G+C contents of 37 to 38 mol %, as expected from previous analysis (DeRosa, et al., 1975; Felsenstein, 1989). No sequence homologs of these ORFs were evident in searches of sequence databases. Within this contig, malA is flanked on the 5' side by an unusual 1-kb intergenic region. It exhibits a G+C content of 30.8 mol %, a value considerably lower than that for the flanking coding regions.

Northern blot analysis of the malA region identified transcripts for malA and an upstream ORF located 5' to the 1-kb intergenic region. The malA transcription start site was located by primer extension analysis (Trienzenberg, 1992) to a guanine residue 8 bp 5' of the malA start codon. Gel mobility shift analysis (Buratowski et al., In Ausubei, et al., 1996) of the malA promoter region suggests that sequences 3' to position about 70 (SEQ ID NO:1) including a consensus archaeal TATA box, play an essential role in malA.

Figure 1B:
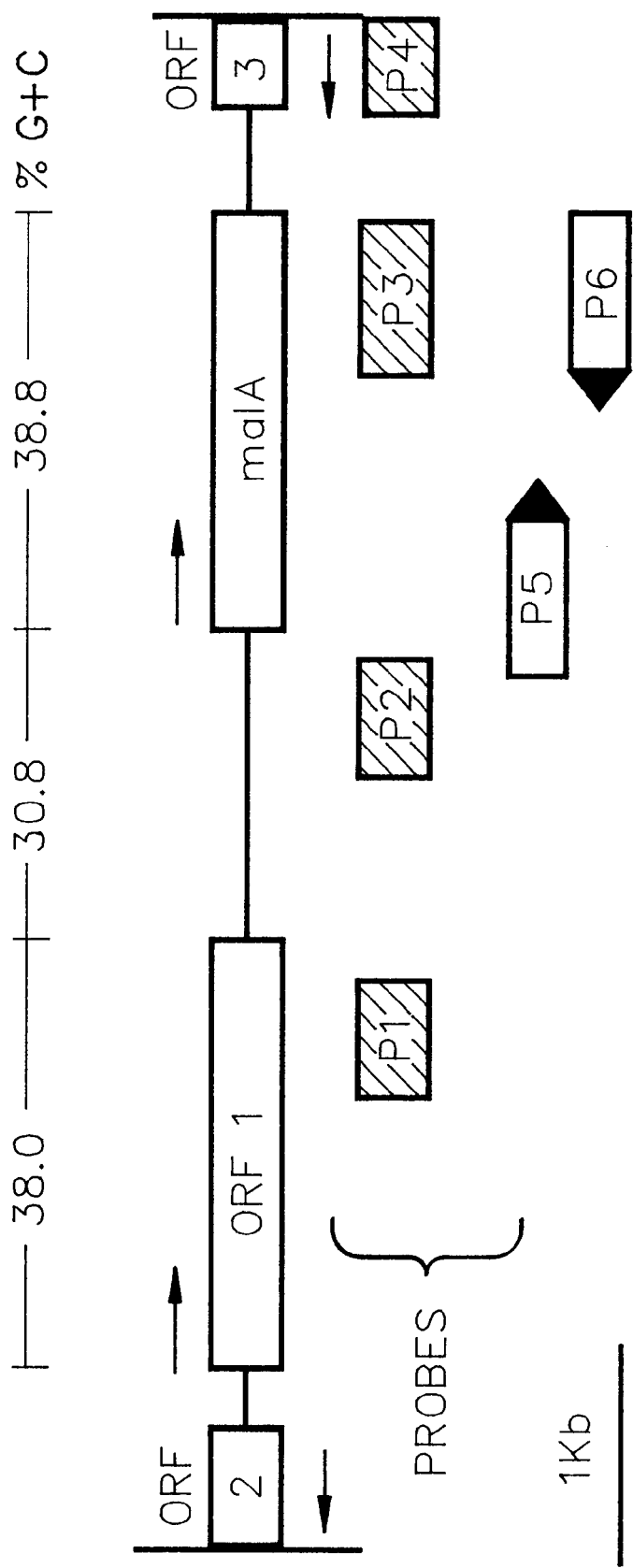

There is a potential archaeal promoter sequence located 32 bp 5' to the start codon of the malA gene (FIG. 1B). The putative promoter (TTTATA) closely matches the consensus promoter sequence for Sulfolobus (Reiter, et al., 1988). A box B motif (TGA) (Reiter, et al., 1988) is also evident 7 bp 5' to the malA start codon. Primer extension analysis indicated that malA transcription initiates on the guanine of the putative box B motif. The mapped start site is 8 bp 5' to the malA start codon. Although there is a potential ribosome binding site spanning positions −3 to +3 (FIG. 2), which are complementary to the six 3'-terminal bases of the 16S rRNA of S. solfataricus (Kurosawa and Itoh, 1993; Zillig, 1993), this sequence overlaps in part the site of malA transcription initiation. The utilization of this sequence for the initiation of translation is therefore unclear. The malA mRNA is only slightly larger than the coding region of the gene. Since transcription initiates very close to the start of the coding region, termination of transcription of the-gene must occur close to the end of malA. The near-consensus terminator sequence (TTTTTCA) (Daalgard, 1983) located immediately 3' to the stop codon of malA may play a role in this process (FIG. 2).

The interaction between purified archaeal TATA binding proteins and archaeal promoters have been characterized by gel shift analysis (Qureshi, 1995). Crude cell extracts prepared as described previously for use in an in vitro transcription system (Hudepohl, et al., 1990) were used as sources of DNA binding proteins. The probe was a 233-bp EcoRI fragment which starts 151 bp 5' to the malA transcription start site and extends 80 bp into the malA transcript. Addition of crude cell extract resulted in the formation of two retarded protein DNA complexes. Both complexes were eliminated by addition of the 233-bp EcoRI malA promoter fragment as an unlabeled competitor DNA. The more rapidly migrating complex (FIG. 4, complex B) was lost in response to addition of competitor-DNA consisting of a 231-bp EcoRI-PvuII fragment from plasmid pUC19, indicating that it was the result of nonspecific interactions. Addition of a competitor DNA comprised of a deletion derivative of the malA EcoRI promoter fragment, lacking sequences from bp −33 to +81, including the TATA box (FIG. 1B, malA p-S), again eliminated only the lower band. These results suggest that sequences located between bp −33 and +81 (FIG. 2) are important features of the malA promoter.

Amino acid sequences of alpha-glucosidases and the related sucrase isomaltases were retrieved from the Swiss-Prot and EMBL/Gen-Bank/DDBJ databases. A multiple sequence alignment of 6 bacterial and 11 eukaryotic sequences in addition to the S. solfataricus sequence was made. The region of the S. solfataricus alpha-glucosidase used for the alignment included 569 amino acid residues spanning positions 50 to 618. The S. solfataricus alpha-glucosidase is the only representative of the archaea, since no other archaeal alpha-glucosidases were found in the databases. A conserved stretch of amino acids located in the middle of the three fungal sequences was deleted to minimize sequence gaps in the alignment. The alignment of sequences then was analyzed by distance, parsimony, and maximum-likelihood methods. The E. coli malZ gene product was used as the outgroup. The sequences clustered into two groups typical of either eubacterial or eukaryotic affiliation, under all three methods of analysis. Nearestneighbor distance analysis and parsimony analysis indicated that the *S. solfataricus* alpha-glucosidase is most closely related to mammalian enzyme homologs. Maximum-likelihood analysis gave similar results.

Example 2

Distribution of the malA Gene Among Sulfolobus Species

Figure 3A:
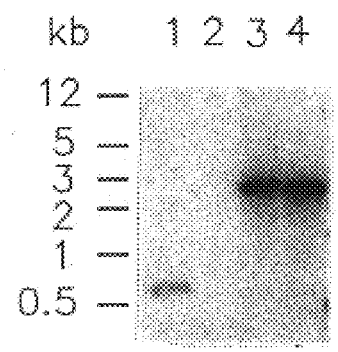
FIGS. 3A and 3B show the distribution of malA DNA among Sulfolobus species as determined by Southern blot.
Figure 3B:
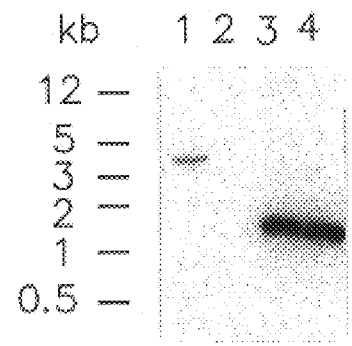

Southern blot analysis with a malA gene probe was performed to analyze the distribution of this gene among the three commonly cultivated Sulfolobus species. Two isolates of *S. solfataricus* were included in the analysis, strain 98/2 from Yellowstone National Park and strain P2 (DSM 1617) from Italy. Genomic digests prepared with EcoRV (FIG. 3A) or HindIII (FIG. 3B) were then probed under stringent hybridization conditions with a 731-bp EcoRV-HindIII malA gene fragment encompassing nucleotides 714 to 1445 of the malA coding region (FIG. 2). Both strains of *S. solfataricus* exhibited strongly hybridizing bands of 2.9 kb following EcoRV digestion and 1.2 kb following HindIII digestion(FIG. 3, lanes 3 and 4), in agreement with the Southern blot results obtained previously with the 731-bp HindIII-EcoRV probe fragment derived from the initial malA PCR product. For *S. shibatae,* single weakly hybridizing bands of 0.65 kb following EcoRV digestion (FIG. 3A, lane 1) and 3.7 kb following HindIII digestion (FIG. 3B, lane 1) were also observed. No cross-hybridization was observed, however, between the *S. solfataricus* malA gene and *S. acidocaldarius* genomic DNA digests (FIGS. 3A and B, lanes 2). Lack of a malA homolog or significant α-glucosidase activity in *S. acidocaldarius* may be due to the inability of *S. acidocaldarius* to utilize maltose as a sole carbon and energy source. (Rolfsmeier, et al. 1998). An alpha-glucosidase thus may be essential for utilization of maltose among certain members of the genus Sulfolobus. This represents a distinguishing physiological feature for Sulfolobus species identification.

Example 3

Isolation of DNA Encoding for Thermostable Alpha-glucosidase from *Sulfolobus solfataricus*

Isolation of DNA encoding thermostable α-glucosidases from hyperthermophilic members of Sulfolobus genus can be accomplished using primers based on the glycosyl hydrolase motif at residues 316 to 323 and the ATP/GTP binding site motif (P loop) at residues 583 to 590 (single underline) as shown in FIG. 2. The amino acid sequence information can be used to design degenerate oligonucleotides which can be used to amplify DNA fragments by PCR. Restriction fragments derived from the PCR products can be used to generate a radio labeled probe for screening genomic or cDNA libraries of Sulfolobus species. Isolates can be identified and restriction fragments can be analyzed for cross-hybridization and sub-cloning. Isolation of malA homologs from other closely related archaea can be accomplished by screening recombinant DNA libraries of the target organism with probes derived from the malA gene. To obtain homologs from more distantly related archaea antibodies can be raised against malA as probes to screen expression libraries.

Example 4

Expression of Recombinant Alpha-glucosidase Activity in *Escherichia coli* and its Purification and Characterization malA gene encoding of hyperthermophilic alpha-glucosidase, was confirmed by expression in *E. coli*. The recombinant enzyme was then purified and characterized.

A 2.1-kb region spanning bp 141 to 2265 (FIG. 2), encompassing the malA coding region and 30 bp of flanking sequence, was blunted and cloned into the SmaI site of pUC19. This construct was then digested with Kpn1 and Pst1, and the resulting 2.1-kb fragment was subcloned into the Kpn1 and Pst1 sites of plasmid pLITMUS 29 (New England Biolabs). The pLTIMUS 29 derivative was then digested with Stu1 and PvuII and religated to itself to remove a T7 promoter located 3' to the malA sequence. The resulting plasmid was introduced into *E. coli* DH5α for production of the recombinant protein by using stationary-phase cell suspensions, typically in 0.5 liter amounts.

Purification of the recombinant enzyme to apparent homogeneity employed heat fractionation of clarified cell sonicates followed by anion-exchange fast protein liquid chromatography and gel filtration fast protein liquid chromatography as described by Rolfsmeier, et al., 1995. The recombinant *S. solfataricus* alpha-glucosidase exhibited significant recalcitrance to denaturation as indicated by its behavior during denaturing SDS-PAGE. Despite boiling in the presence of 2% (wt/vol) SDS for 10 minutes, the alpha-glucosidase failed to enter the separating gel and instead migrated in significant amounts (representing 45% of the total observed protein) in the stacking gel. However, 95% of the natural enzyme treated in an identical manner was in the multimeric form (Rolfsmeier, et al., 1995), suggesting that the recombinant enzyme dissociates more readily under these conditions. Complete denaturation of the recombinant alpha-glucosidase required additional treatment with 6 M guanidine hydrochloride, resulting in exclusive formation of the 80-kDa monomer. Assays for alpha-glucosidase activity with p-nitrophenyl-α-D-glucopyranoside were performed as described by Rolfsmeier, et al., 1995. In enzymatic assays for hydrolysis of maltose and glycogen, release of glucose was monitored with a glucose oxidase assay kit (Sigma) as described by Rolfsmeier, et al., 1995.

Increasing expression is accomplished by changing codons which are not heavily used in the host species, whether microbial or plant. Codon usage tables are available for many plant hosts, including tobacco, thus the identification of which codons to change and what to change them to as well as the method to do it are well known in the art.

Figure 4A:
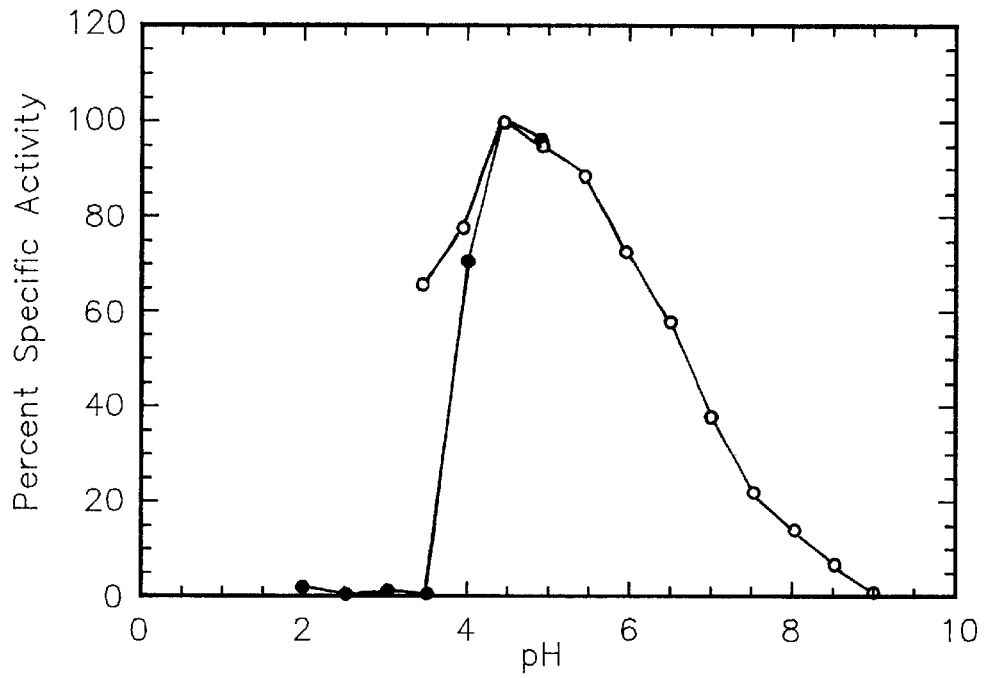
FIGS. 4A and 4B show the pH optima of recombinant alpha-glucosidase for maltose and glycogen hydrolysis.
Figure 4B:
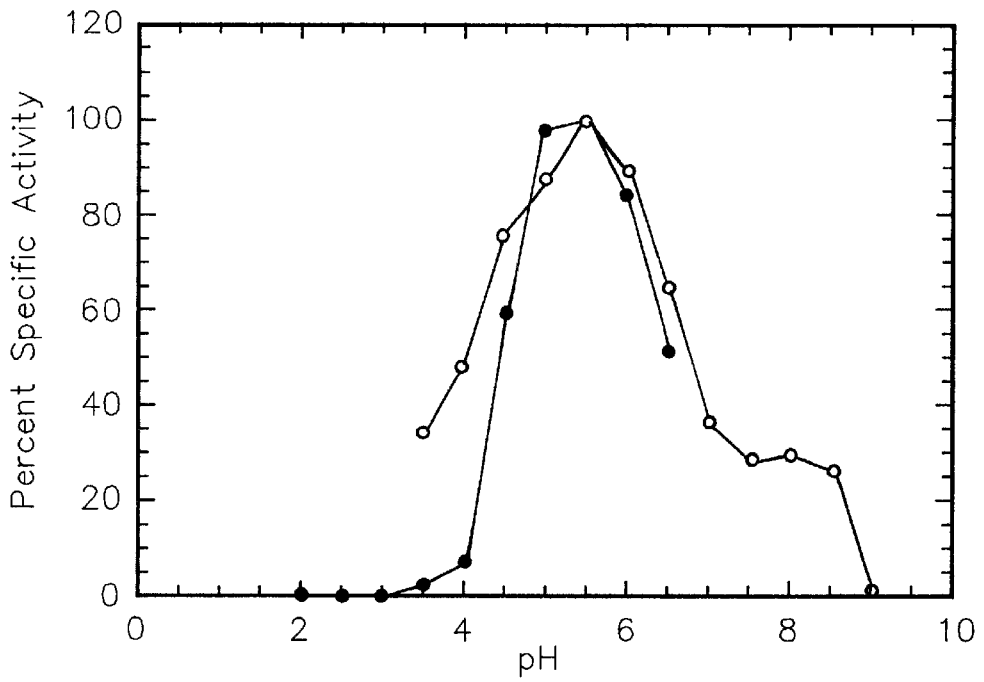

The purified, recombinant enzyme hydrolyzes p-nitrophenyl-α-D-glucopyranoside with a Km of 2.16 mM and a $V_{max}$ of 3.08 μmol of p-nitrophenol/min at 85° C. It exhibited a pH optimum for maltose hydrolysis of 4.5 (FIG. 4A). In contrast to its apparent greater tendency to dissociate during SDS-PAGE, the recombinant alpha-glucosidase exhibits greater thermostability than the natural enzyme with a half-life of 39 h at 85° C. at a pH of 6.0. The half-life for the natural enzyme is 11 h at 85° C. (Rolfsmeier et al., 1995).

Alpha-glucosidases of mammalian origin are generally distinguished from those of higher plants and eubacteria by their affinities for glycogen as a substrate. Surprisingly, glycogen is hydrolyzed efficiently by alpha-glucosidase from *S. solfataricus*. The recombinant alpha-glucosidase exhibits a pH optimum for glycogen hydrolysis of 5.5 (FIG. 4B), a Km of 64.9 mg/ml, and a $V_{max}$ of 1.0 μmol of glucose/min at 85° C.

Recombinant enzyme purification of beta-glycosidase was performed using transformants of *E. coli* DH5α (Gibco-BRL) harboring the lacS expression plasmid pBN55. The strain was grown at 37° C. with vigorous shaking in 4 liters of LB medium containing ampicillin (100 μg/ml) until the cells reached stationary phase. Cells were harvested by centrifugation, resuspended in 30 mM morpholinepropane-sulfonic acid, pH 8.0 (MOPS buffer) and lysed by sonication at 4° C. The resulting lysates were clarified by centrifugation (3,000×g for 30 min.) and then heated at 85° C. for 30 min. and reclarified by centrifugation. The heating and centrifugation procedure was then repeated a second time. The heat-treated supernatants were concentrated by ultrafiltration using a YM3 (Amicon) membrane.

The concentrated supernatants were applied to a Mono Q FPLC (fast protein liquid chromatography) column (Parmacia) previously equilibrated with MOPS buffer. The recombinant β-glycosidase was eluted with linear gradients of sodium chloride in MOPS buffer. Active fractions of the enzyme were identified by enzyme assay, pooled, concentrated by ultrafiltration using a PM10 (Amicon) membrane, and dialyzed into 100 mM sodium phosphate buffer (pH 6.0). The dialyzed samples were applied to a Superdex 200 HR 10/30 FPLC column (Pharmacia) previously equilibrated with 100 mM sodium phosphate (pH 6.0). Active fractions were again pooled and concentrated by ultrafiltration.

Example 5

Transformation of Tobacco Plants by Agrobacterium tumefaciens Transformed with a Binary Plasmid Containing the malA or lacS Genes During the cloning of the malA gene into the plant vector, candidate colonies were screened by growing overnight in LB broth containing the appropriate antibiotic, pelleting the cells and resuspending them in 0.1 M sodium acetate at pH 4.5. Assay for alpha-glucosidase was performed with para-nitrophenyl-α-D-glucopyranoside as described in Rolfsmeier, et al., 1995. In order to construct the binary plasmid, the malA gene which had been cloned from a genomic library of Sulfolobus solfataricus strain 98/2 (pBN56; Rolfsmeier et al., 1998), containing the coding sequence and about 30 bp of 5' flanking sequence, was first cloned into the vector pGEM 7Zf+ (Promega) to pick up useful restriction sites. The malA open reading frame and 30 bp lying both 5' and 3' was then cloned between the enhanced 35S promoter (5') and the 35S polyadenylation site (3') of the pRTL2 plasmid which was provided by J. C. Carrington, after the TEV leader sequence (Carrington and Freed, 1990; Carrington, et al., 1990) had been removed by digestion with Xho I and Bam HI. The resulting expression cassette was subcloned into the multiple cloning site of the binary vector pPZP112 (Hajdukiewicz, et al., 1994)at the Pst I site (near right T-DNA border) to produce the construct pPB709, shown in FIG. 1. The pPZP112 vector contains the neomycin phosphotransferase (NPT II) gene under the 35S promoter within the T-DNA near the left border, resulting in a plasmid in which the gene of interest inserts first into the genome (Hajdukiewicz, et al., 1994). The lacS gene including its bacterial expression system and antibodies were as described in Haseltine, et al., 1999(a). A pPZP112 derivative expressing lacS was constructed using the same strategy as described for malA.

The resulting binary vector plasmid constructs were used to transform Agrobacterium tumefaciens strain C58C1 by the freeze-thaw method (An et al., 1988). The bacteria was then used to transform tobacco (Nicotiana tabacum cv. Xanthi) by the leaf disk method (Horsch et al., 1985). Rooted regenerants were identified as transformants by detection of NPT II in leaf tissue with the ELISA kit (5 Prime 3 Prime, Inc.), according to the manufacturer's instructions.

After transformation and regeneration of tobacco leaf disks with vector containing the malA or lacS gene, 17 rooted tobacco regenerants were identified by their positive reaction on NPT II ELISA as having been transformed with the T-DNA from Agrobacterium tumefaciens containing the gene.

Based on the methods described herein and the data presented, those of skill in the art would be able to construct plants expressing both glycosyl hydrolases.

Example 6

Preparation of Enzyme Concentrate from Tobacco Extract

To obtain tobacco leaf extract for assays, approximately 100 g of tobacco (five 1.1 cm diameter disk punches) leaves were harvested, rinsed with distilled water, midribs removed and weighed. Leaves were then ground to a powder in liquid nitrogen and ground again with a sterilized pestle. The extracts were then clarified by centrifugation at 14,000 rpm for 10 minutes at room temperature. The resulting supernatant was heat treated for 1 hour at 85° C. and clarified by spinning at 14,000 rpm for 10 minutes at room temperature. The supernatant was collected and assayed for alpha-glucosidase or beta-glycosidase enzyme activity by measuring the hydrolysis of p-nitrophenyl-alpha-glucopyranoside (alpha-PNPG) and p-nitrophenyl-beta-D-glucopyranoside (beta-PNPG), respectively, as previously described (Rolfsmeier, et al., 1998; Haseltine, et al., 1999(a)). Plant tissue extracts for studies on hydrolysis of added defined substrates were prepared using 100 g of tobacco leaves were harvested and grinded to a fine powder in liquid nitrogen. The leaf powder was resuspended in 500 ml of 10 mM tris-Cl pH7.0 to which 10 mM beta-mercaptoethanol has been added. The suspension was then homogenized in a Waring blender. The resulting extract was centrifuged at 5,000 rpm for 30 minutes at 4° C. and the supernatant was further clarified by filtering through three layers of cheesecloth. Plant extracts used for studies on hydrolysis of endogenous polysaccharides as sources of transgenic proteins were prepared using one leaf (medium to large) for each plant which was harvested and ground to a fine powder in liquid nitrogen. The ground leaves were resuspended in 2 volumes of 100 mM sodium phosphate pH 7.0 with 10 mM beta-mercaptoethanol and the tissue was further homogenized in a Waring blender. The resulting extracts were then incubated at 80° C. to activate the recombinant alpha-glucosidase and beta-glycosidase for 48 hours. After incubation, the extracts were clarified by centrifugation by 12,500 rpm for 10 minutes 4° C. Glucose released by glycosyl hydrolase action on endogenous plant carbohydrates was measured using the Glucose Oxidase Assay (Sigma).

Example 7

Detection of Recombinant Alpha-glucosidase and Beta-glycosidase Activity in Nicotiana tabacum and Determination of its Substrate Specificity Assays of recombinant alpha-glucosidase from concentrated tobacco extract used by alpha-linked para-nitrophenlglucoside (Sigma) or 4-methylumbelliferyl-α-D-glucoside (4-MUG) (Sigma) as substrates at concentrations of 1 mM in 0.05M sodium acetate buffer at pH 4.5. Total protein was quantified using the Bradford protein assay kit from BioRad (Bradford, 1976). Extract was incubated one hour at 85° C. and re-clarified to remove any endogenous tobacco alpha-glucosidase. Extract and substrate were pre-warmed for 10 minutes then combined in a reaction volume of 300 ul, layered with 150 ul mineral oil and incubated 3 hours at 85° C. Aliquots of 25 ul were removed after zero and three hours of incubation and transferred to stop solution consisting of 1 M $Na_2CO_3$. The reaction product, 4-methylumbelliferone, was detected on a DyNAQuant 200 fluorometer. Each extract was assayed in duplicate. Routine assays of beta-glycosidase were performed as described by Haseltine, et al., 1999(a).

Tobacco leaf extracts to be used for detection of glycosyl hydrolase antigens were concentrated 3-fold by $(NH_4)_2 SO_4$ precipitation. Western blot analysis followed protocols from Sambrook, et al., 1989. Preparations were made 1× in SDS-PAGE sample buffer and 30 ug total protein per well was oaded on a 12% SDS polyacrylamide gel (8% stacking) and electrophoresed ccording to Haseltine, et al., 1999(b). Proteins (Amersham) were transferred to nitrocellulose and incubated. Chemiluminescent (colorimetric) western blots were performed as described by Rolfsmeier, et al., 1998. The recombinant E coli extracts used as controls for the alpha-glucosidase and the beta-glycosidase on western blots were prepared as previously described (Haseltine, et al., 1999(b)). Concentrated plant protein extracts were diluted 1:10 in 10 mM tris-Cl pH 7.0. 50 ul of anti-malA antibodies were added to 200 ul of diluted extract and incubated for 2 hours at 4° C. with gentle agitation. After incubation, an equivalent of 350 µg of protein A was added and the mixture was incubated for 3 hours at 4° C. and the supernatant was collected and assayed for alpha-glucosidase activity using the MUG assay. Blots were soaked with a chemiluminescent substrate solution (Amersham) and results visualized by autoradiography and quantified by densitometry.

The substrate 4-MUG broke down at 85° C., pH 4.5, to form fluorescent product at about the same rate in the presence or absence of tobacco leaf extract made from plants transformed with the empty vector pPZP112. When 1 mM 4-MUG was incubated with extract from a plant transformed with the malA gene, the rate of product formation was close to six times the rate of product formation in the presence of extract made from empty vector control. Fluorescence due to endogenous compounds in tobacco extracts was unchanged for four hours at 85° C.

Figure 5A:
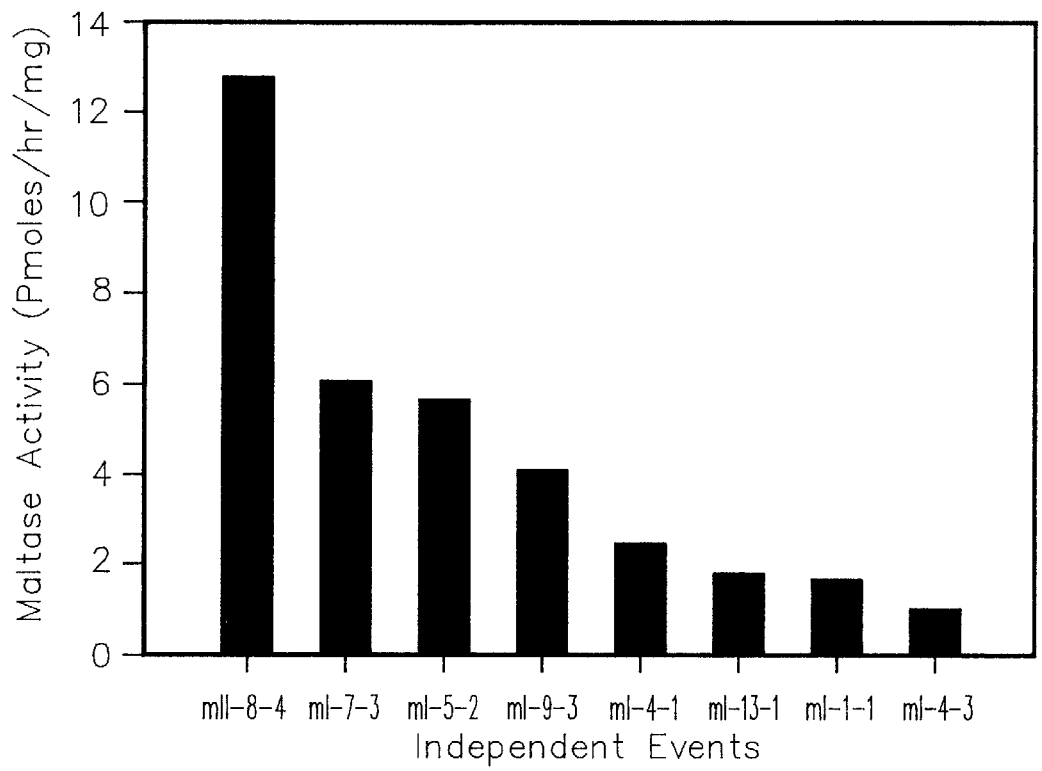
FIGS. 5A and 5B show levels of thermostable glycosyl hydrolases in transgenic tobacco transformants.
Figure 5B:
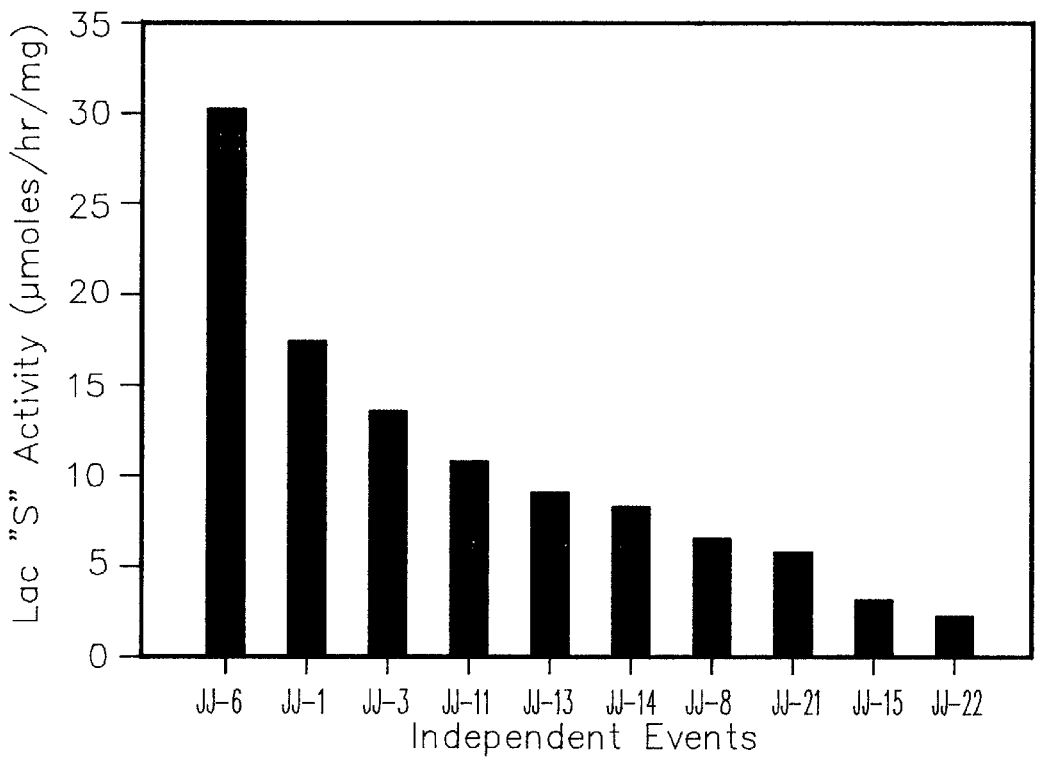
Figure 6:
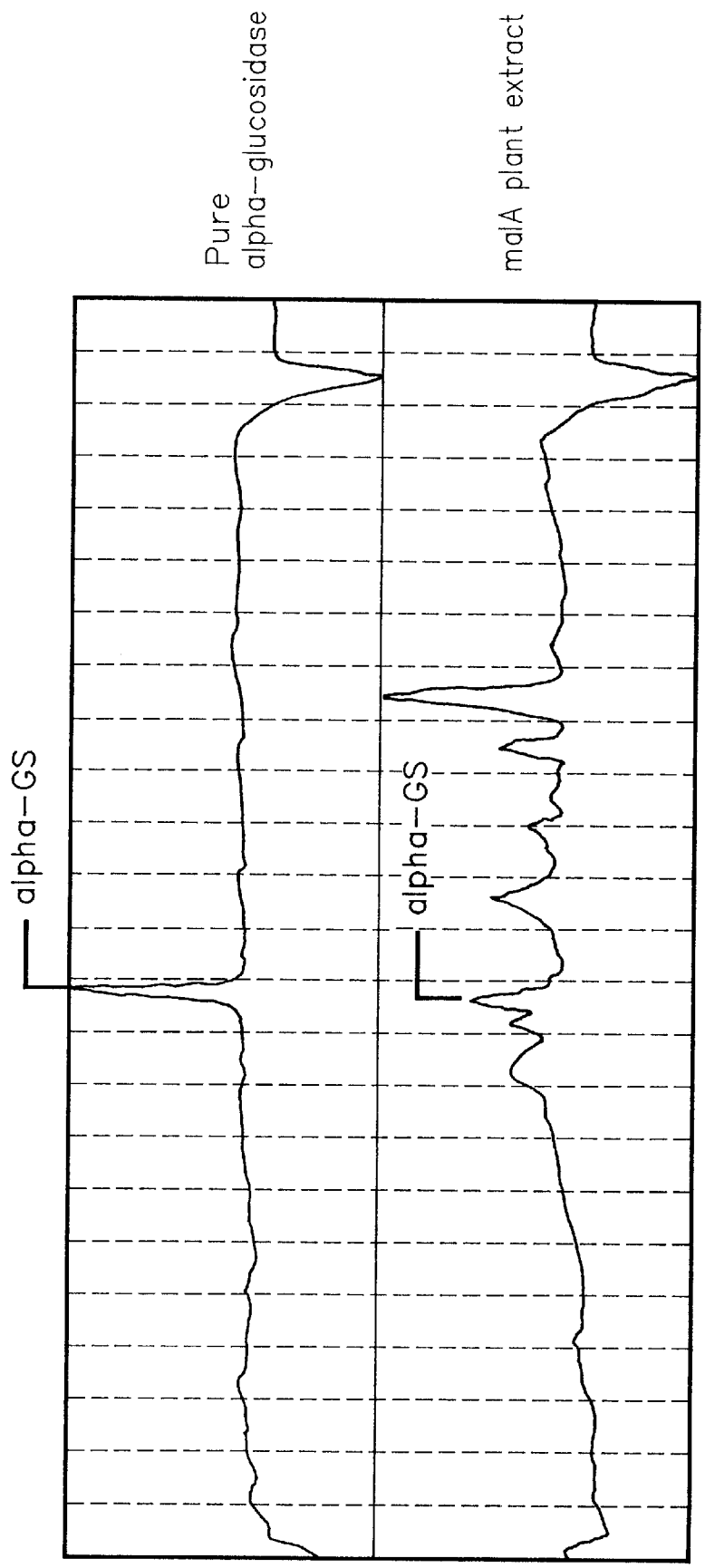
FIG. 6 shows a densitometry tracing of a western blot of malA plant extract and purified alpha-glucosidase.

Glucosyl hydrolase levels were determined in primary plant transformants using clarified leaf extracts incubated at 80° C. Plants transformed with empty vector lacked detectable thermostable glycosyl hydrolase activity. Activity was measured on fully expanded leaves of plants that had grown in soil for 76 to 164 days. Levels of the beta-glycosidase in young primary transformants was determined in twenty-three independent events. Enzyme levels in ten representative isolates ranged over 12-fold with maximum values of 29 µmoles PNP/min/mg of protein (FIG. 5B). Eight representative isolates of twenty-two independent events exhibited enzyme specificity over a 13-fold range with maximum values of 13 pmoles PNP/hr/mg protein (FIG. 5A).

Figure 12A:
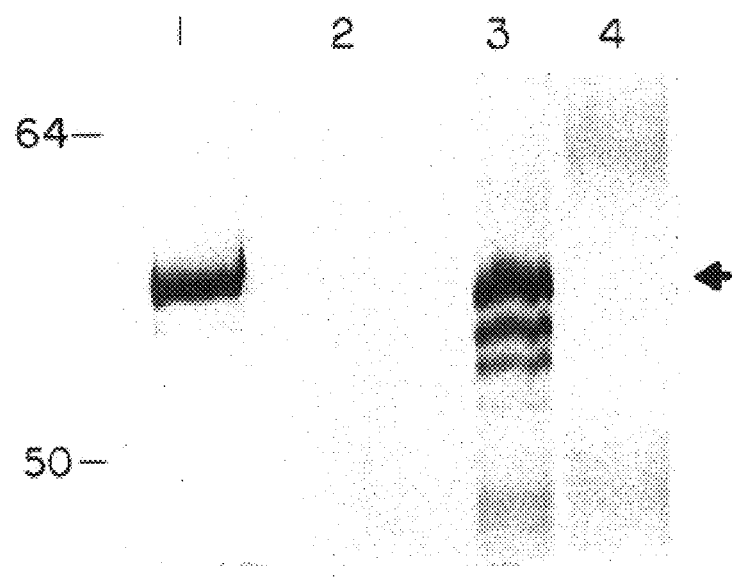
FIGS. 12A, 12B and 12C show the presence of glycosyl hydrolases in transformed tobacco leaves.
Figure 12B:
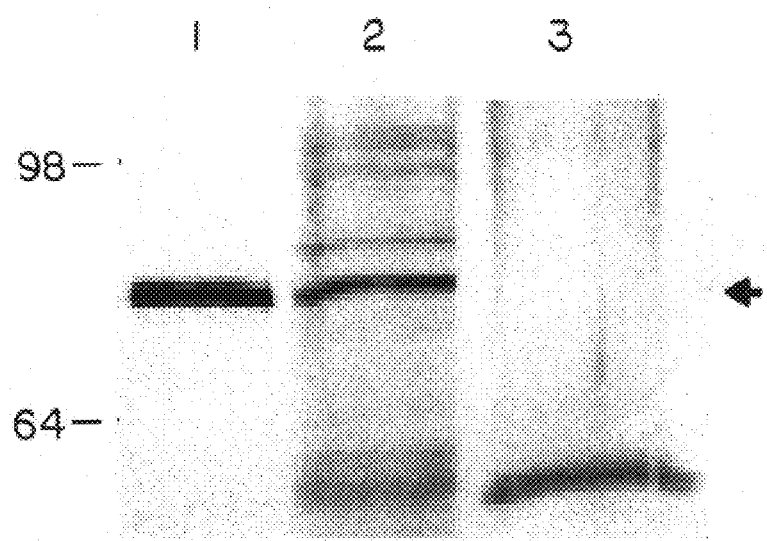

The protein identity of the thermostable glycosyl hydrolase activities was confirmed by western blot analysis of plant extracts (FIG. 12). Western blot analysis of plant extracts derived from the T2 plant JJ-6, transformed with the lacS gene, detected a protein with an apparent mass of 60 kDa (FIG. 12B, lane 1). No cross-reacting material was evident in extracts from a plant transformed with an empty vector (lane 2). Recombinant beta-glycosidase produced using a recombinant E. coli expression strain (Sunna, 1997) was used as a positive control for these experiments. Degradation of this material is apparent and resulted from proteolysis during preparation of the E. coli extract. No cross-reacting material was evident in whole cells extracts from E. coli lacking the lacS expression plasmid (lane 3). Similar results were obtained for plants transformed with the malA gene expression construct (FIG. 12A). Recombinant alpha-glucosidase protein produced using a recombinant E. coli expression strain (Sunna, 1997) was used as a positive control (FIG. 12A, lane 1). A protein with an apparent mass of 80 kDa and identical to the positive control sample mass was detected in extracts of the T2 plant MI52E but not in extracts of the plant transformed with the empty vector (lanes 2 and 3, respectively).

Precipitation of tobacco leaf proteins with $(NH_4)_2 SO_4$ achieved a 3-fold concentration of the recombinant alpha-glucosidase with a recovery of 100%. Endogenous plant glycolytic activities were eliminated prior to malA assays by heat inactivation (1 hr, 55° C.). Background due to endogenous glucose was removed by dialysis. Initial attempts to assay concentrated extract from tobacco transformed with malA vector or empty vector, with or without 5% starch as substrate, failed to demonstrate activity in the malA tobacco extract due to a very high background in the presence of the starch. In an attempt to remove this background, concentrated empty vector control extract was pre-incubated for one hour at 85° C., clarified by microcentrifugation and then incubated for 0 or 14 hour at 85° C. in the presence or absence of 5% starch. Without preincubation, background in the presence of starch was very high, at both 0 and at 14 hours, corresponding to 17.8 to 19.2 micrograms of glucose per 100 microliters of assay. Background in the absence of starch was much lower, but apparently more time-dependent, rising from 0.9 to 1.6 micrograms of glucose per 100 microliters in 14 hours (FIG. 7). When the extract was pre-heated before assay, the background in the absence of starch was unchanged, but the background in the presence of starch was then at the same level as the background in the absence of starch without pre-heating (FIG. 7). Based on these results, the very high background appears to have been due to one or more endogenous tobacco enzymes active at room temperature, and acting on added starch during the interval between combining the reaction components and transferring reaction mixes from 250 to 85° C. The background in the absence of added starch might have been due to nonenzymatic degradation of an endogenous glucose polymer, or due to formation of compounds that interfere with the glucose oxidase assay.

As with the empty vector extract, the background in the absence of starch was lower than the background in the presence of added starch, rising from 1.3 to 5.3 micrograms of glucose per 100 microliters in 16 hours, and was not affected by pre-treatment of one hour at 85° C. (FIG. 7). The background in the presence of added starch was greatly reduced by the one-hour pre-treatment, but was dependent on incubation time at 85° C., and was still substantially greater than the background in the absence of added starch, rising from 2.0 to 10.2 micrograms of glucose per 100 microliters in 16 hours. The net rate of glucose formation, which is believed to represent the conversion of added starch to glucose by the recombinant alpha-glucosidase, was 0.42 micrograms per hour (FIG. 7).

Figure 12C:
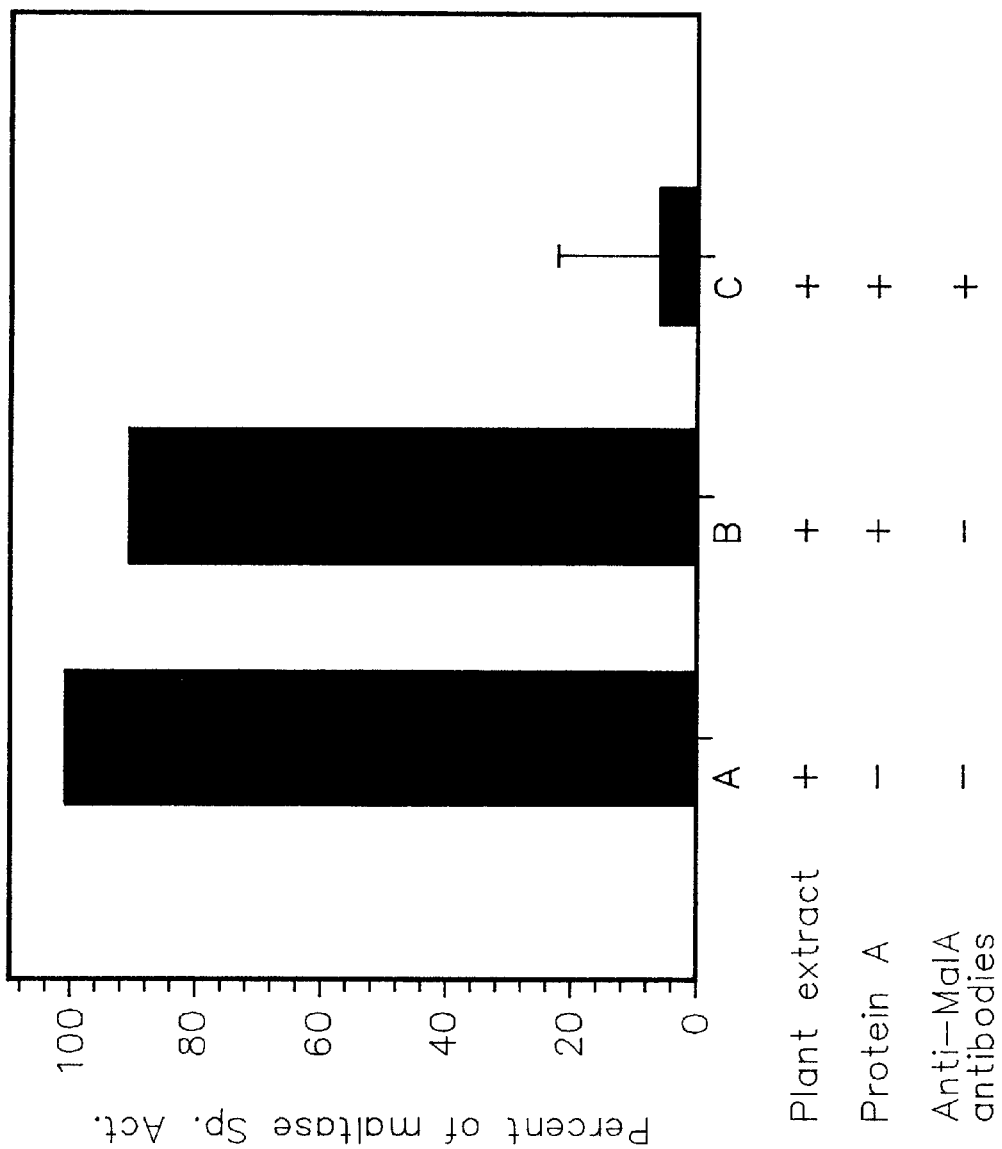

Since significantly greater amounts of plant extract were required to detect the alpha-glucosidase compared to the beta-glycosidase, additional experiments using protein immunoprecipitation were conducted to further confirm alpha-glucosidase production (FIG. 12C). A sample of T2 plant MI52E extract was treated with the anti-alphaglucosidase antibody and antibody-antigen complexes were removed by Staphylococcus protein-A treatment. The residual activity remaining in the treated samples was then determined by enzyme assay. Additional samples of T2 plant MI52E extract treated with Staphylococcus protein A alone or with no treatment were also analyzed for residual alpha-glucosidase activity. Nearly complete removal of alpha-glucosidase was evident in samples treated with the anti-alpha-glucosidase antibodies but not in untreated samples or in samples treated only with protein A. The results verify production of the thermostable glycosyl hydrolases in tobacco leaves.

For measurements of glycosyl hydrolase activities on glucose polymers. An equal volume of −20° C. acetone was added to extract, followed by storage at −20° C. for one hour and centrifugation for 30 minutes at 10,000×g (GSA rotor, r.p.m.). Pellets were lyophilized, then resuspended with about 1/100 the original volume of 10 mM tris HCl pH 7 and clarified by microcentrifugation. After incubating one hour at 85° C. and reclarifying, extracts were lyophilized to remove free glucose and small solutes that could interfere with the glucose oxidase assay. Assays of alpha-glucosidase on starch used soluble potato starch (from Fluka) at 5% (w/v) in 0.05 M sodium acetate buffer, pH 4.5. Aliquots of 100 ul were removed at four hour intervals and glucose was detected with a glucose oxidase glucose detection kit from Sigma.

The recombinant alpha-glucosidase from tobacco was active on maltose and a number of other α-(1→4) linked glucose polymers, as shown in Table 1. This demonstrates that the recombinant hydrolases of the present invention are useful for release of other sugars in addition to glucose.

TABLE 1

Substrate Specificity of the
Sulfolobus solfataricus α glucosidase

| Substrate[a] | Specific Activity (μmoles glucose/min/mg) |
| --- | --- |
| Maltose | 3.32 ± 0.46 |
| Maltotriose | 1.17 ± 0.26 |
| Maltotetrose | 1.91 ± 0.61 |
| Maltoheptose | 1.48 ± 0.00 |
| Sucrose[b] | 1.29 ± 0.03 |
| Dextrin (1% w/v) | 0.85 ± 0.04 |
| Starch (1% w/v)[b] | 4.75 ± 0.5 |
| Starch (5% w/v)[b] | 8.67 ± 0.0 |
| Glycogen (1% w/v)[b] | 0.52 ± 0.07 |
| Glycogen (5% w/v)[b] | 3.75 ± 0.3 |

[a]Substrate concentrations were 10 mM except dextrin, starch and glycogen which were performed at the concentrations listed. Assays were performed 30 minutes at 80° C.
[b]Indicates the assay was performed with the recombinant enzyme.

Example 8

Expression and Accumulation of Recombinant Glycosyl Hydrolases by Second Generation Tobacco Plants T2 were obtained by screening seed for kanamycin resistant germination. Single copy transgene insertions were identified as yielding kanamycin resistance segregation frequencies of 3:1 in T3 seed. T2 plants harboring single insertions from several independent lines were used for detailed experiments. Of the 17 NPT II-positive tobacco plants, nine had sufficient levels of the alpha-glucosidase to be detected with reasonable certainty. Recovery of tobacco plants producing the beta-glycosidase occurred at frequencies similar to those of the alpha-glucosidase.

Figure 11A:
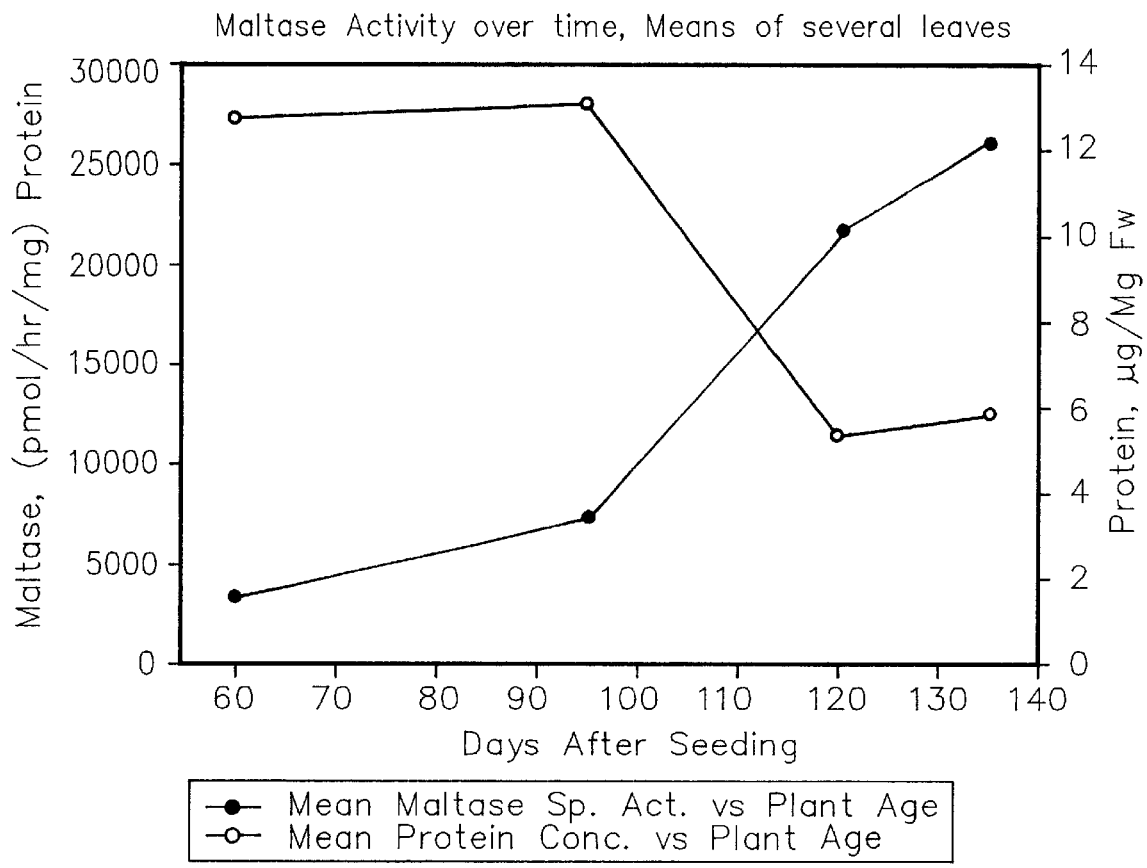
FIGS. 11A and 11B show accumulation of recombinant glycosyl hydrolase activities in aging transgenic tobacco plants.
Figure 11B:
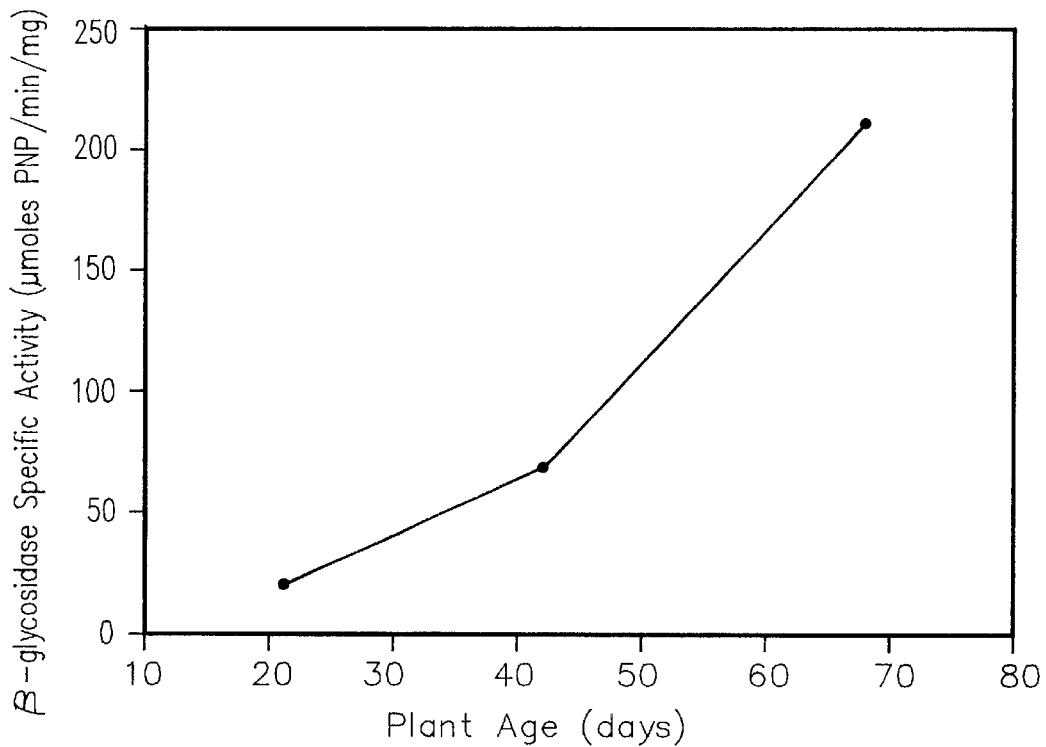

Analysis of enzyme levels in fully expanded leaf tissue samples from identical T2 plants collected over time indicated that the glycosyl hydrolase activities increased as the plants matured (FIG. 11). Total protein was measured on both a fresh weight and leaf area basis. In contrast to the expected pattern observed with most transgenic proteins (Sunna, 1997), levels of the alpha-glucosidase were low in younger plants and reached appreciable levels as plants aged and following flower formation (FIG. 11B). Total protein levels in contrast were most elevated in younger plants and decreased significantly as the plants aged. A similar novel pattern of accumulation was observed for transgenic plants producing the beta-glycosidase (FIG. 11A).

Example 9

Stability of Recombinant Glycosyl Hydrolases in Preserved Plant Tissue

It has been determined that glycosyl hydrolases retain significant activity in fully mature and preserved leaf tissue. Glycosyl hydrolase specific activities in plant tissues were compared, after freezing or drying, to levels in fresh tissue samples (Table 2). Significant beta-glycosidase activity was retained in leaves harvested and held at −80° C. for 5 days. In contrast, the alpha-glucosidase activity was over two times more stable when frozen and 17 times more stable when dried, as compared to fresh tissues.

The retention of transgenic glycosyl hydrolase activities in preserved plant tissues confirms that the plant tissue can be stored for later use as a source of hydrolase activity. This means that crops traditionally used for forage would be useful and appropriate hosts since they are left in the field until after winter.

TABLE 2

Stability of Recombinant Glycosyl Hydrolases in Preserved Plant Tissue

| Condition | Beta-glycosidase (μmoles PNP/min/mg) | Alpha-glucosidase (μmoles PNP/hr/mg) |
| --- | --- | --- |
| Frozen | 67 | 3.6 |
| Dried | 31 | 27 |
| Fresh | 62 | 1.6 |

Example 10

Autodigestion of Plant Substrates by Thermostable Enzymes

Figure 7A:
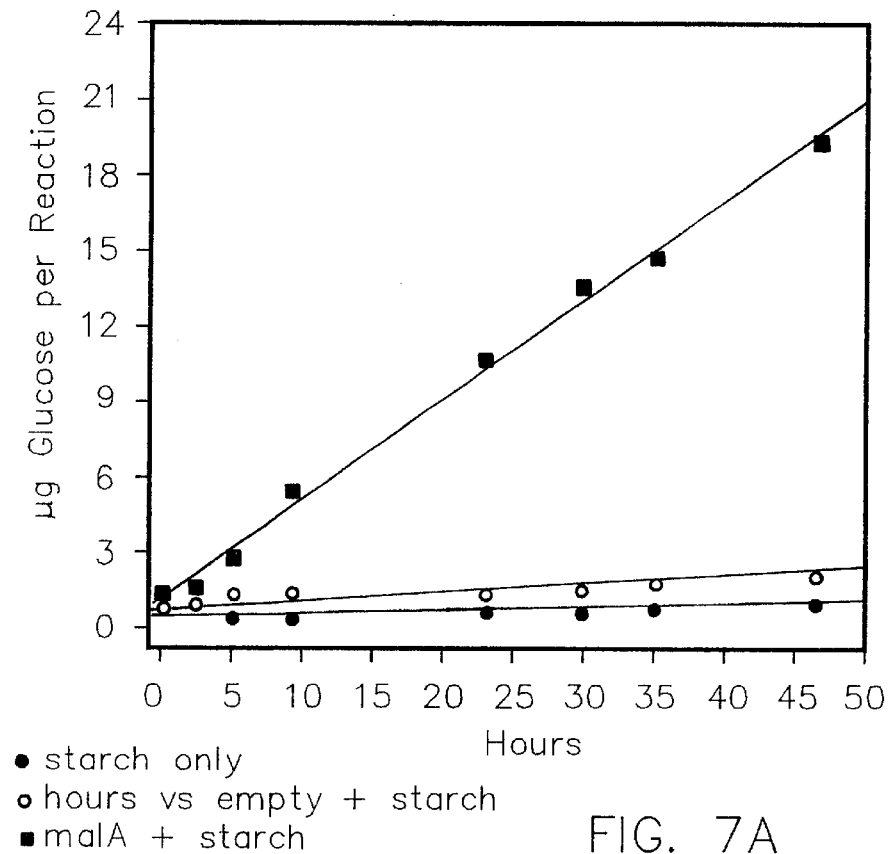
FIGS. 7A and B show the release of glucose by transgenic glycosyl hydrolases from exogenous and endogenous plant carbohydrates.
Figure 7B:
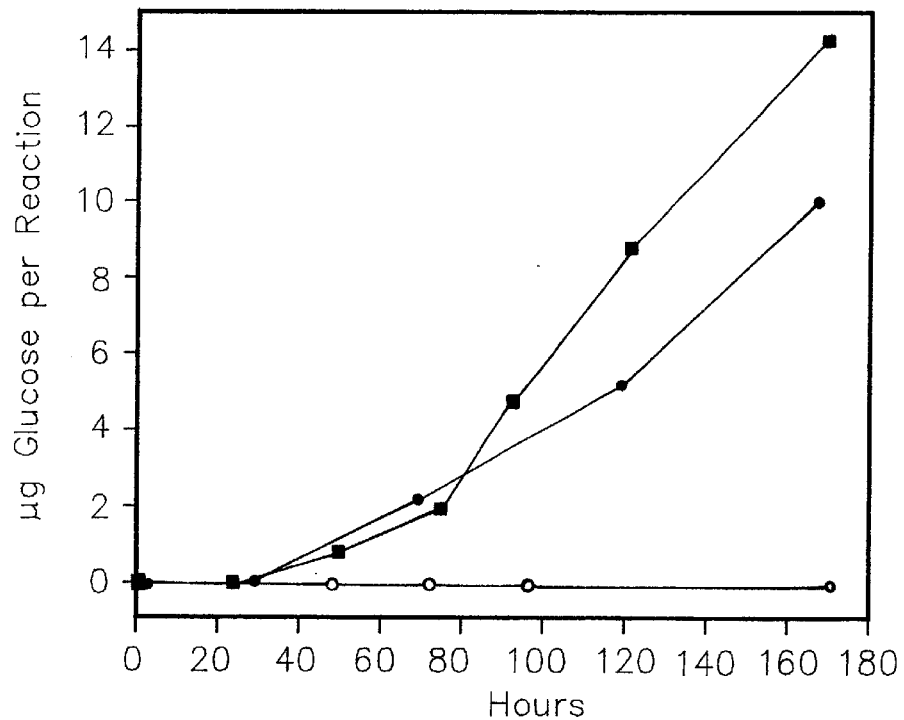
FIG. 7B. Glucose released by glycosyl hydrolases using an endogenous polysaccharide-enriched plant extract as substrate. Protein extracts were: beta-glycosidase (closed squares), alpha-glucosidase (closed circles), and empty vector transformed plant (labeled). Glucose levels were determined using the glucose oxidase assay.
Figure 8B:
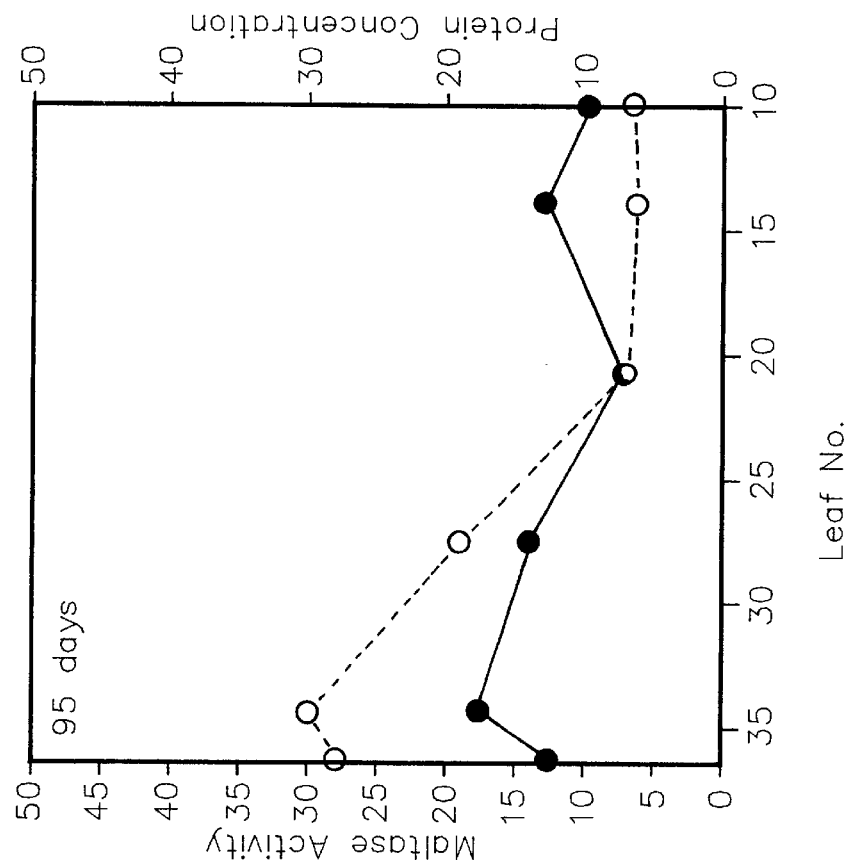
FIGS. 8A, 8B and 8C are plots of recombinant alpha-glucosidase activity and protein content per milligram fresh weight in leaves of T2 tobacco plants at 70, 95 and 116 days after seeding, respectively.
Figure 8A:
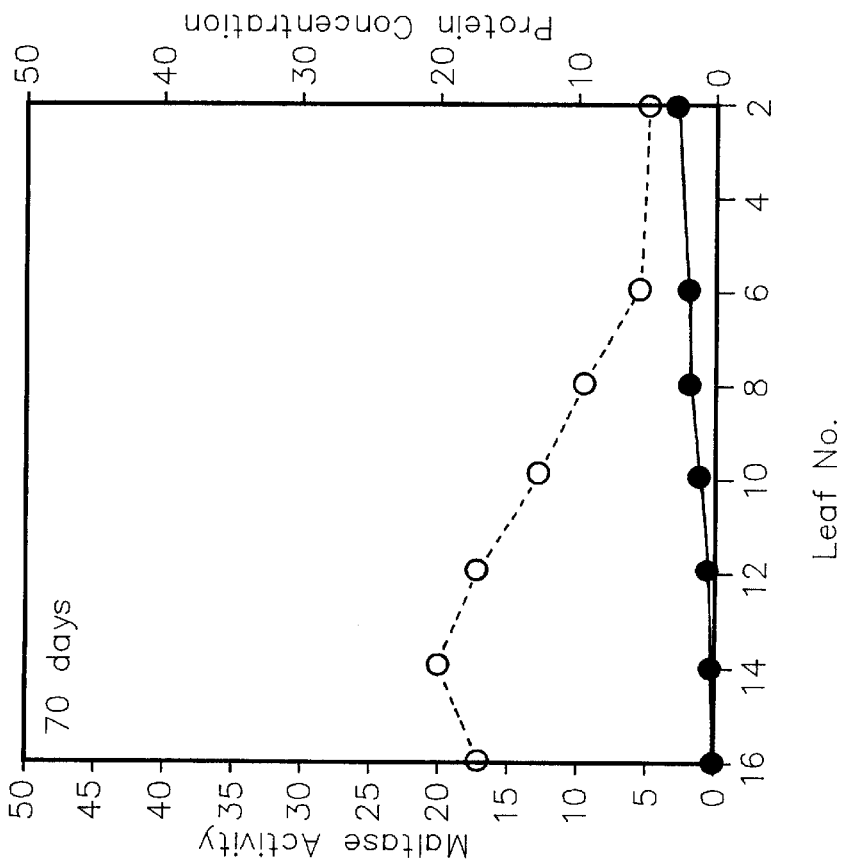
Figure 8C:
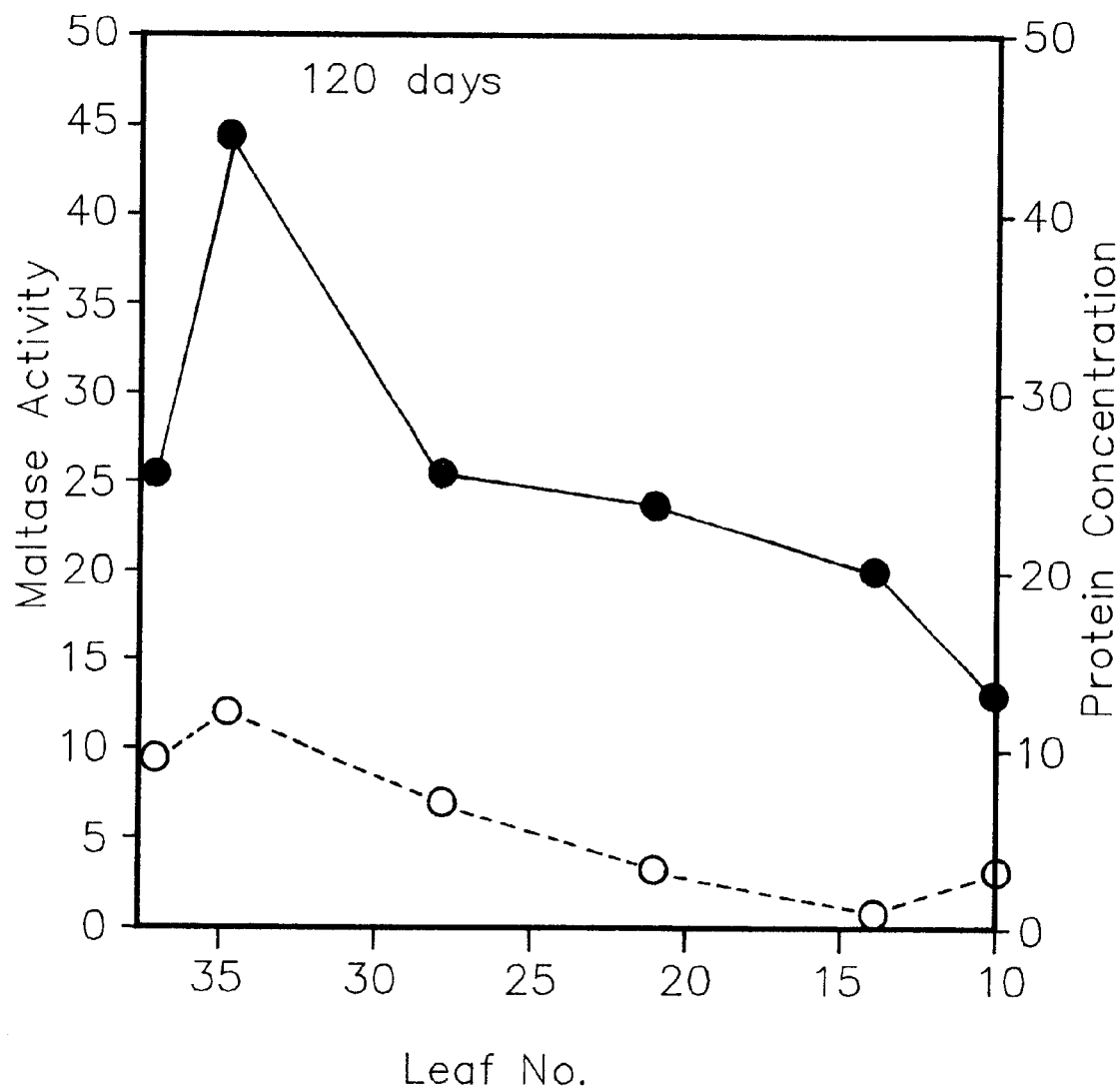
Figure 9A:
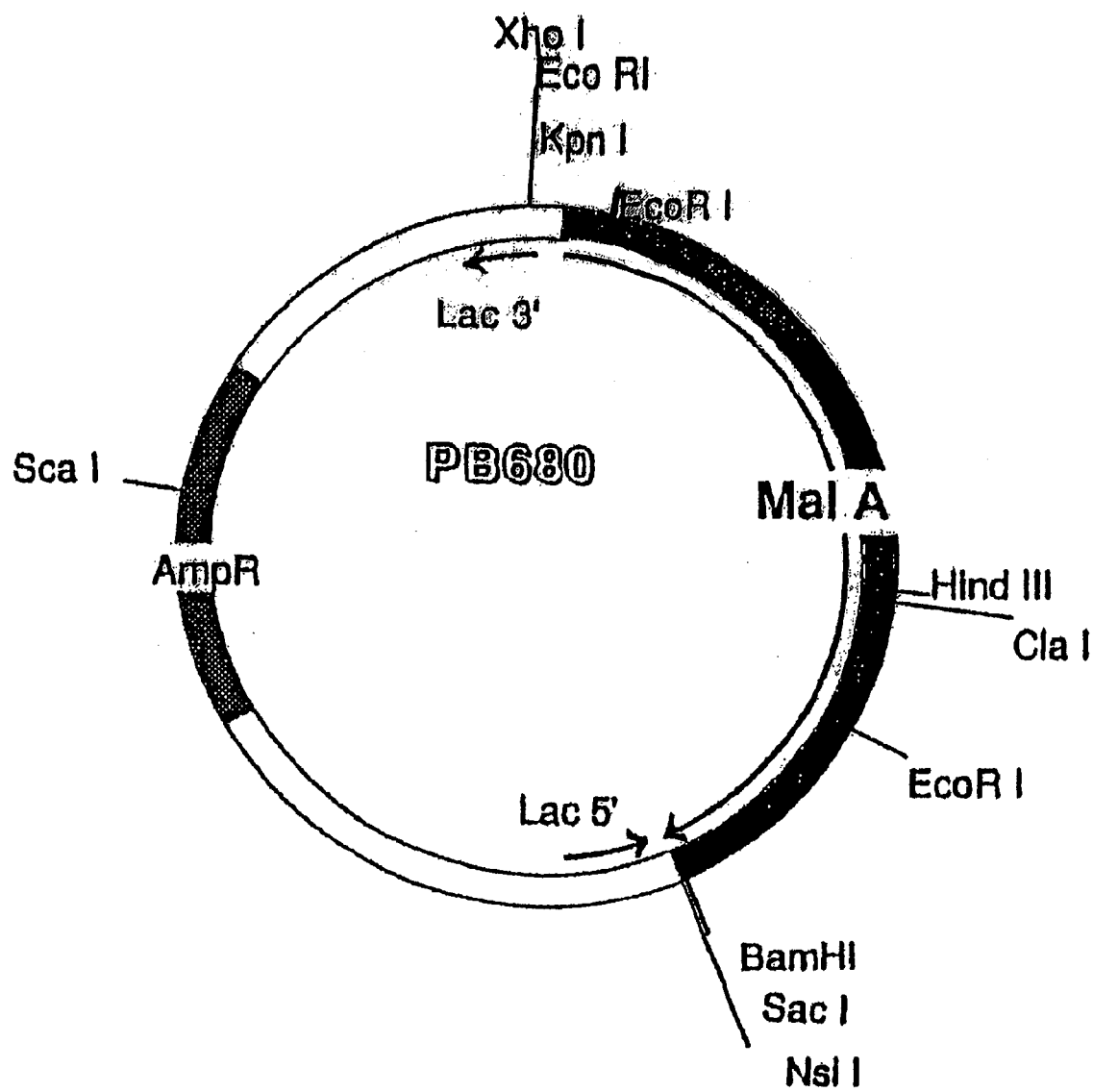
FIGS. 9A and 9B. 9A shows the bacterial expression vector including the malA gene. 9B is a Northern blot of the malA region of the vector.
Figure 9B:
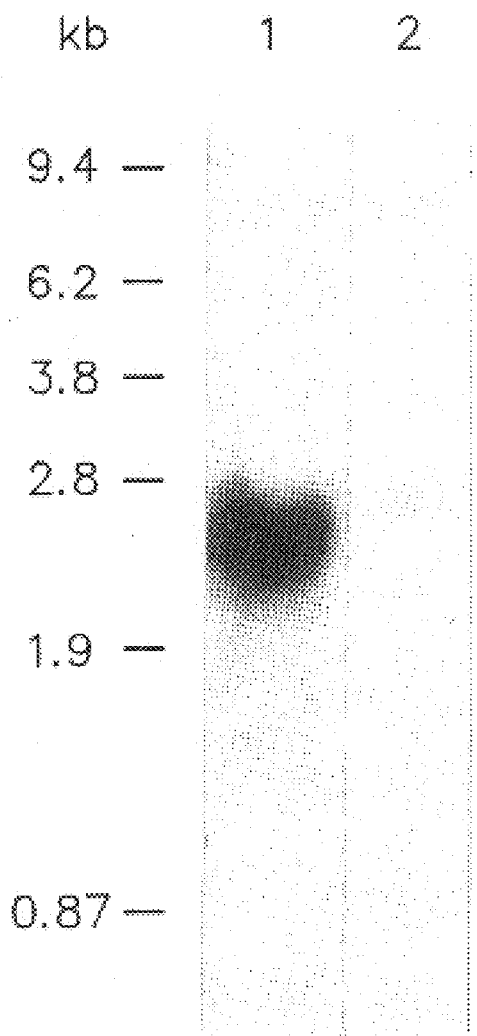
Figure 10A:
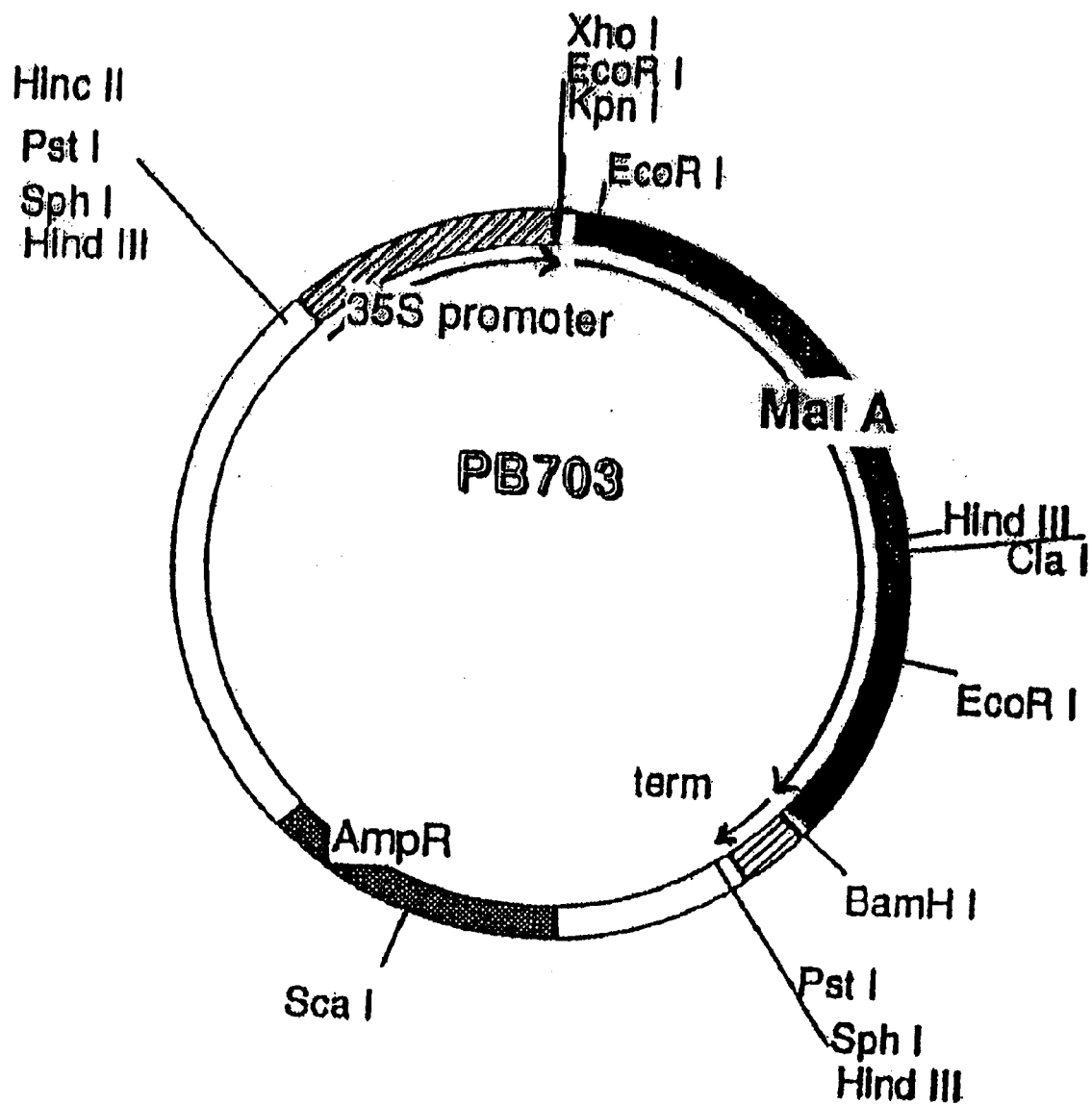
FIGS. 10A and 10B. 10A shows the plant expression plasmid including the malA gene. 10B is a Northern blot of the malA region of the plasmid.
Figure 10B:
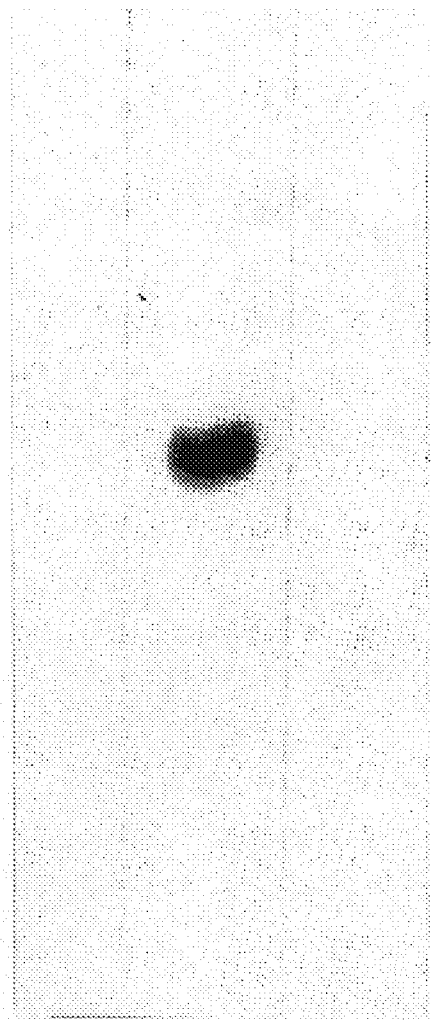

Conversion of plant polysaccharide into free sugar is conventionally done by addition of purified or semipurified hydrolytic enzymes. As an example of the use of endogenous thermostable enzymes for plant bioprocessing, the ability of plant protein extracts to hydrolyze polysaccharides such as starch was demonstrated (FIGS. 7A and 7B). Protein extracts of the alpha-glucosidase transgenic plant MI52E, were prepared and combined with soluble starch. Plant leaves were harvested in the late afternoon, ground in liquid nitrogen with a mortar and pestle in 100 mM phosphate buffer at pH 7.0. Upon incubation at 80° C., glucose was released in a manner which was collinear with time. No significant glucose was detected in reactions containing protein extracts from plants transformed with empty vector and added starch or in reactions containing starch alone. The rate of appearance of glucose was 0.11 μg/hr for alpha-glucosidase and 0.15 μg/hr for beta-glucosidase. These results demonstrated that glycosyl hydrolase in plant protein extracts could depolymerize added exogenous soluble starch.

To demonstrate the use of endogenous plant polysaccharides as substrates for the transgenic glycosyl hydrolases, transgenic tobacco protein extracts were combined with tobacco extracts processed to enrich for polysaccharide content (Sunna, 1997). Levels of liberated glucose were determined as a function of incubation time at 80° C. After an initial lag of 28 hr., levels of glucose began to increase in extracts containing either the alpha-glucosidase or the beta-glycosidase. In contrast, glucose levels did not increase in reactions containing the polysaccharide enriched extracts and a protein extract from plants transformed with an empty vector. Glucose release continued for the duration of the experiment which was terminated after 160 hr. These results demonstrate that transgenic levels of the glycosyl hydrolases are sufficient to catalyze hydrolysis of endogenous polysaccharide using extracts separately enriched for proteins and substrate.

Direct conversion of plant tissue into sugar without resort to extract fractionation (autodigestion) was examined by high temperature incubation of crude unfractionated transgenic plant extracts. To better assess the amount of sugar released by autodigestion of transgenic plant tissue, the resulting preparations were used as growth media for the cultivation of bacteria. Crude extracts of plants transformed with malA and lacs genes were prepared, incubated at 80° C., then clarified. $E.$ $coli$ K12 cells ($10^7$) were washed and inoculated into flasks containing the clarified extracts. The flasks were incubated overnight at 37° C. Control flasks were prepared with extract from plants transformed with the empty vector. Both glycosyl hydrolase plant extracts supported high cell density growth of $E.$ $coli$ K12 while a plant transformed with an empty vector did not. The ratio of microbial biomass produced from transgenic glycosyl hydrolase plants was examined by determining the microbial growth yield on a per volume basis of incubated plant crude extract. When beta-glycosidase and alpha-glucosidase crude extracts we recombined microbial biomass yields were proportionally greater.

While the invention has been disclosed in this patent application by reference to the details of preferred embodiments of the invention, it is to be understood, that the disclosure is intended in an illustrative rather than in a limiting sense, as it is contemplated that modifications will readily occur to those skilled in the art, within the spirit of the invention and the scope of the appended claims.

LIST OF REFERENCES

Allen, M. B. (1959). "Studies with Cyanidium caldarium. an anomalously pigmented chlorophyte." *Arch Mikrobiol.* 32:270–277.

An, G., et al. (1988). "Binary Vectors." In Gelvin, S. B., et al. (Eds.), *Plant Mol. Bio. Manual.* A3:1–19, Kluwer Academic Publishers, Dordrecht, Netherlands.

Birnboim, H. C., and J. Doly (1979). "A rapid alkaline extraction procedure for screening recombinant plasmid DNA." *Nucleic Acids Res.* 7:1513–1523.

Blum, P. J., et al. (1992). "Physiological consequences of DnaK and DnaJ overproduction in *Escherichia coli.*" *J. Bacteriol.* 174:7436–7444.

Bradford (1976). *Anal. Biochem.* 72:1248–1254.

Bragger, J. M., et al. (1989). "Very stable enzymes from extremely thermophilic archaebacteria and eubacteria." *App. Microbiol.* 31:556–561.

Brock, T. D., et al. (1972). "Sulfolobus: a genus of sulfur oxidizing bacteria living at low pH and high temperature." *Arch. Mikrobiol.* 84:54–68.

Brown, T., and K. Mackey (1997). "Analysis of RNA by Northern and slot blot hybridization. unit 4.9.1–4.9.13." In F. M. Ausubel, et al. (eds). *Current protocols in molecular biology.* John Wiley and Sons, Inc., New York, N.Y.

Buratowski, S., and L. A. Chodosh (1996). "Mobility shift DNA-binding assay using gel electrophoresis, unit 12.2.1–12.2.7." In F. M. Ausubel, et al. (eds). *Current protocols in molecular biology.* John Wiley and sons. Inc. New York.

Burggraf, S., et al. (1997). "Reclassification of the crenarchaeal orders and families in accordance with 16S rRNA sequence data." *Int. J. Syst. Bacteriol.* 47:657–660.

Carrington, J. C., et al. (1990). "Cap-independent enhancement of translation by a plant potyvirus 5' untranslated region." *J. Virol.* 64:1590–1598).

Carrington, J. C., et al. (1990). "Expression of potyviral polyproteins in transgenic plants reveals three proteolytic activities required for complete processing." *EMBO J.* 9:1347–1353.

Chomczynski, P., and N. Sacchi (1987). "Single-step method of RNA isolation by acid guanidinium thiocyanate-phenol-chloroform extraction." *Anal. Biochem.* 162:156–159.

Costantino, H. R., et al. (1990). "Purification and characterization of an alpha-glucosidase from a hyperthermophilic archaebacterium. *Pyrococcus furiosus.* Exhibiting a temperature optimum of 105 to 115 degrees Celsius." *J. Bacteriol.* 172:3654–3660.

Cowan, D. A. (1992). "Biotechnology of the Archaea." *Trends Biotechnol.* 10(9):315–23.

Cubellis, M. V., et al. (1990). "Isolation and sequencing of a new β-glucosidase-encoding archaebacterial gene." *Gene.* 94:89–94.

Daalgard, J. Z., and R. A. Garret (1993). "Archaeal hyperthermophile genes," pp. 535–563. In M. Kates, et al. (eds)., *The biochemistry of Archaea.* Elsevier Science Publishers. New York, N.Y.

Dennis, P. P. (1986). "Molecular biology of archaebacteria." *J. Bacteriol.* 168: 471–478.

De Rosa, M., et al. (1975). "Extremely thermophilic acidophilic bacteria convergent with *Sulfolobus acidocaldarius.*" *J. Gen. Microbiol.* 86:156–164.

Felsenstein, J. (1989). "PHYLIP-phylogeny inference package (version 3.2)." *Cladistics* 5:164–166.

Grogan, D., et al. (1990). "Isolate B12, which harbours a virus-like element. represents a new species of the archaebacterial genus Sulfolobus, *Sulfolobus shibatae.*" sp. nov. *Arch. Microbiol.* 154:594–599.

Grogan, D. W. (1989). "Phenotypic characterization of the archaebacterial genus Sulfolobus: comparison of five wild-type strains." *J. Bacteriol.* 171:6710–6719.

Grogan, D. W. (1991). "Evidence that B-galactosidase of *Sulfolobus solfataricus* is only one of several activities of a thermostable B-D-glycosidase." *Appl. Environ. Microbiol.* 57:1644–1649.

Hajdukiewicz, P., et al. (1994). "The small, versatile pPZP family of Agrobacterium binary vectors for plant transformation." *Plt. Mol. Biol.* 25:989–994.

Hanahan, D. (1983). "Studies on transformation of *Escherichia coli* with plasmids.) *J. Mol. Biol.* 166:557.

Haseltine, C., et al. (1999(a)). "Coordinate transcriptional control in the hyperthermophilic archaeon *Sulfolobus solfataricus.*" *J. Bacteriol.* 181:3920–3927.

Haseltine, C., et al. (1999(b)). "Extragenic Pleiotropic Mutations That Repress Glycosyl Hydrolase Expression in the Hyperthermophilic Archaeon *Sulfolobus solfataricus.*" *Genetics* 1353–1361.

Haseltine, C., et al. (1996). "The glucose effect and regulation of a-amylase synthesis in the hyperthermophilic arcaeon *Sulfolobus solfataricus.*" *J. Bacteriol.* 178:945–950.

Hensel, L. L., et al. (1993). "Developmental and age-related processes that influence the longevity and senescence of photosynthetic tissues in arabidopsis." *Plant Cell.* 5(5):553–64.

Hermans, M. M. P., et al. (1991). "Human lysosomal a-glucosidase." *J. Biol. Chem.* 266:13507–13512.

Hers, H. G. (1963). "a-Glucosidase deficiency in generalized glycogen-storage disease (Pompe's disease)." *Biochem. J.* 86:11–16.

Hochstein, L. I., and H. Stan-Lotter (1992). "Purification and properties of an ATPase from *Sulfdobus solfataricus.*" *Arch. Biochem. Biophys.* 295:153–160.

Horsch, R. B., et al. (1985). "A simple and general method for transferring genes into plants." *Science* 227:1229–1231.

Huber, G., and K. O. Stetter. 1991. "*Sulfolobus metallicus.* sp. nov., a novel strictly chemolithoautotrophic thermophilic archaeal species of metal-mobilizers." *Syst. Appl. Microbiol.* 14:372–378.

Hudepohl, U., et al. (1990). "In vitro transcription of two rRNA genes of the archaebacterium Sulfolobus sp. B12 indicates a factor requirement for specific initiation." *Proc. Natl. Acad. Sci. USA* 87:5851–5855.

Kandler, O., and K. O. Setter (1981). "Evidence for autotrophic $CO_2$ assimilation in *Sulfolobus brierleyi* via a reductive carboxylic acid pathway, Zentralbl." *Bakteriol. Hyg. Abt.* 1 *Orig.* C2:111–121.

Kelly, C. T., and W. M. Fogarty (1983). "Microbial a-glucosidases." *Process Biochem.* 18:6–12.

Kondo, S., et al. (1991). "Positive selection for uracil auxotrophs of the sulfur-dependent thermophilic archaebacterium *Sulfolobus acidocaldarius* by use of 5-fluoroorotic acid." *J. Bacteriol.* 173:7698–7700.

Konig, H., et al. (1982). "Glycogen in thermoacidophilic archaebacteria of the genera Sulfolobus. Thermoproteus. Desulfurococcus and Thermococcus." *Arch. Microbiol.* 132:297–303.

Krska, J., et al. (1993). "Monoclonal antibody recognition and function of a DnaK (HSP70) epitope found in gram-negative bacteria." *J. Bacteriol.* 175:6433–6440.

Kurosawa, N., and Y. H. Itoh (1993). "Nucleotide sequence of the 16S rRNA gene from thermoacidophilic archaea *Sulfolobus acidocaldarius* ATCC33909." *Nucleic Acids Res.* 21:357.

Lamppa, G., et al. (1985). "Light-regulated and organ-specific expression of a wheat Cab gene in transgenic tobacco." *Nature.* 316(6030):750–2.

Lubben, M., and G. Schafer (1989). "Chemiosmotic energy conversion of the archaebacterial thermoacidophile *Sulfolobus acidocaldarius:* oxidative phosphorylation and the presence of an $F_o$-related N,N'-dicyclohexylcarbodiimide-binding proteolipid." *J. Bacteriol.* 171:6106–6116.

Matsudaira, P. (1990). "Limited N-terminal sequence analysis." *Methods Enzymol.* 182:602–613.

McWethy, S. J., and P. A. Hartman (1979). "Extracellular maltase of *Bacillus brevis.*" *Appl. Environ. Microbiol.* 37:1096–1102.

Mitushara, I., et al. (1996). "Efficient promoter cassettes for enhanced expression of foreign genes in dicotyledonous and monocotyledonous plants." *Plant Cell Physiol.* 37:49–59.

Nucci, R., (1993). "Exoglucosidase activity and substrate specificity of the B-glycosidase isolated from the extreme thermophile *S. solfataricus.*" *Biotechnol. Appl. Biochem.* 17:239–250.

Olsen. G. J., et al. (1985). "Sequence of the 16S rRNA gene from the thermoacidophilic archaebacterium *Solfataricus solfataricus* and its evolutionary implications." *Mol. Evol.* 22:301–307.

Qureshi, S. A., et al. (1995). "Cloning and functional analysis of the TATA binding protein from *Solfataricus shibatae.*" *Nucleic Acids Res.* 23:1775–1781.

Reiter, W. D., et al. (1988). "Analysis of transcription in the archaebacterum Sulfolobus indicates that archaebacterial promoters are homologous to eukaryotic pol II promoters." *Nucleic Acids Res.* 16:1–19.

Rockabrand, D., et al. (1995). "An essential role for the *Escherichia coli* DnaK protein in starvation-induced thermotolerance, $H_2O_2$ resistance, and reductive division." *J. Bacteriol.* 177:3695–3703.

Rockabrand, D., et al. (1995). "Multicopy plasmid suppression of stationary phase chaperone toxicity in *Escherichia coli* by phosphogluconate dehydratase and the N-terminus of DnaK." *Mol. Genet.* 249:498–506.

Rolfsmeier, M., et al. (1998). "Molecular Characterization of the α-Glucosidase Gene (malA) From the Hyperthermophilic Archaeon *Solfolobus solfataricus.*" *J. of Bacteriol.* 180:1287–1295.

Rolfsmeier, M., et al. (1995). "Purification and characterization of a maltase from the extremely thermophilic crenarchaeote *Solfolobus solfataricus.*" *J. Bacteriol.* 177:482–485.

Sambrook, J., et al. (1989). "Molecular cloning: a laboratory manual," 2nd ed. Cold Spring Harbor Laboratory Press, Cold Spring Harbor, N.Y.

Sensen, C. W., et al. (1996). "Organizational characteristics and information content of an archaeal genome: 156 kb of sequence from *S. solfataricus* P2." *Mol. Microbiol.* 5:1687–1693.

Strimmer, K., et al. (1996). "Quartet puzzling: a quartet maximum likelihood method for reconstruction tree topologies." *Mol. Biol. Evol.* 13:964–969.

Sunna, A., et al. (1997). "Glycosyl hydrolases from hyperthermophiles." *Extremophiles* 1(1):2–13.

Takayanagi, S., et al. (1996). "*Sulfolobus hakonensis* sp. nov., a novel species of acidothermophilic archaeon." *Int. J. Syst Bacteriol.* 46:377–382.

Thompson, J. D., et al. (1994). "CLUSTAL W: improving the sensitivity of progressive multiple sequence alignment through sequence weighting, positions-specific gap penalties and weight matrix choice." *Nucleic Acids Res.* 22:4673–4680.

Trent, et al. (1991). *Nature* 354:490–493.

Triezenberg, S. J. (1992). "Primer extension, unit 4.8.4." In F. M. Ausubel, R. Brent, R. E. Kingston, D. D. Moore, J. G. Seidman, J. A. Smith, and K. Struhl (ed), current protocols in molecular biology, John Wiley and Sons, Inc., New York, N.Y.

Urlab, H., et al. (1978). "a-Glucosidase, a membrane-bound enzyme of a-glucan metabolism in *Bacillus amyloliquefaciens.*" *Biochem. Biophys. Acta* 522:161–173.

Wang, L. H., et al. (1976). "Purification and some properties of an extracellular maltase from *Bacillus subtilis.*" *Appl. Environ. Microbiol.* 31:108–118.

Wistler, et al. (1984) (Paschall). *Starch: Chemistry and Technology* Vol. II 1:1–51 Academic Press, Inc., New York, N.Y.

Woese, C., et al. (1990). "Towards a natural system of organisms: proposal for the domains archaea, bacteria and eucarya." *Proc. Natl. Acad. Sci. USA* 87:4576–4579.

Wood, A. P., (1987). "Autotrophic growth of four Sulfolobus strains on tetrathionate and the effect of organic nutrients." *Arch. Microbiol.* 146:382–389.

Yallop, C. A., et al. (1996). "Nutrient utilization and transport in the thermoacidophilic archaeon *Sulfolobus shibatae*." *Microbiology* 142:3373–3380.

Yanez, et al. (1986). "Amaranthushupochondriacus: Starch esolation and partial characterization." *Cereal chemistry*, 63:3,273–277.

Yeats, S., et al. (1982). "A plasmid in the archaebacterium *Sulfolobus acidocaldarius*." *EMBO J.* 1 :1035–1038

Zillig, W. (1993). "Confusion in the assignments of Sulfolobus sequences to Sulfolobus species." *Nucleic Acids Res.* 21:5273.

Zillig, W., et al. (1994). "Screening for Sulfolobales, their plasmids and their viruses in Icelandic solfataras." *Syst. Appl. Microbiol.* 16:609–628.

I claim:

1. A method for converting plant substrate, comprising heating said substrate in the presence of recombinant hyperthermophilic glycosyl hydrolase, wherein said substrate comprises extract of plant transformed with said recombinant hyperthermophilic glycosyl hydrolase, and wherein the glycosyl hydrolase is localized with the substrate in tissue of the plant.

2. The method of claim 1, wherein said plant substrate further comprises a plant extract enriched for said substrate content.

3. The method of claim 1, wherein said hyperthermophilic glycosyl hydrolase is from Sulfolobus species.

4. The method of claim 3 wherein said Sulfolobus species is selected from the group consisting of S. solfataricus 98/2, S. shibatae, S. acidocaldarius, and S. solfataricus P2.

5. The method of claim 1, wherein said hyperthermophilic glycosyl hydrolase is selected from the group consisting of hyperthermophilic alpha-glucosidase, hyperthermophilic beta-glycosidase and combinations thereof.

6. The method of claim 5, wherein said hyperthermophilic glycosyl hydrolase is hyperthermophilic alpha-glucosidase.

7. The method of claim 5, wherein said hyperthermophilic glycosyl hydrolase is hyperthermophilic beta-glycosidase.

8. The method of claim 1 wherein said plant substrate comprises polysaccharide.

9. The method of claim 1, wherein said substrate is heated at a temperature of between about 65° C. and about 85° C.

* * * * *

UNITED STATES PATENT AND TRADEMARK OFFICE
CERTIFICATE OF CORRECTION

| | | |
|---|---|---|
| PATENT NO. | : 6,506,592 B1 | Page 1 of 1 |
| APPLICATION NO. | : 09/376343 | |
| DATED | : January 14, 2003 | |
| INVENTOR(S) | : Paul Blum | |

It is certified that error appears in the above-identified patent and that said Letters Patent is hereby corrected as shown below:

In column 1 after the paragraph referencing the related applications in the Specification, please insert the following statement which should read
--Statement Regarding Federally Sponsored Research and Funding: This invention was made with U.S. Government support under Grant Nos. MCB9604000 and EPS9255225 awarded by the National Science Foundation. The government has certain rights in this invention.--

Signed and Sealed this

Twenty-sixth Day of February, 2008

JON W. DUDAS
*Director of the United States Patent and Trademark Office*

SEQUENCE LISTING

<160> NUMBER OF SEQ ID NOS: 4

<210> SEQ ID NO 1
<211> LENGTH: 2280
<212> TYPE: DNA
<213> ORGANISM: Sulfolobus solfataricus
<220> FEATURE:
<221> NAME/KEY: CDS
<222> LOCATION: (172)..(2250)

<400> SEQUENCE: 1

```
taggaattat cgaattcaac gcttttccaa taaatactaa ttggtttaaa cttaacgtta      60
tgtagttagt tattgtcata atccgaaaaa aggataacaa tctagttgtt taggataaac     120
tagataaagg aagctttata ttttgaagag aattgtatac ggtgataagg g atg cag     177
                                                          Met Gln
                                                            1 aca ata aaa ata tac gag aac aaa ggc gtt tac aaa gta gtt ata gga      225
Thr Ile Lys Ile Tyr Glu Asn Lys Gly Val Tyr Lys Val Val Ile Gly
        5                  10                  15 gaa cca ttt ccc ccc ata gaa ttc cca ctt gag caa aag ata tca tcg      273
Glu Pro Phe Pro Pro Ile Glu Phe Pro Leu Glu Gln Lys Ile Ser Ser
 20                  25                  30 aat aaa tct tta tca gag ttg ggt tta aca ata gtt caa caa ggt aac      321
Asn Lys Ser Leu Ser Glu Leu Gly Leu Thr Ile Val Gln Gln Gly Asn
 35                  40                  45                  50 aag gtt att gtc gag aaa tca ttg gat ttg aaa gag cac att ata gga      369
Lys Val Ile Val Glu Lys Ser Leu Asp Leu Lys Glu His Ile Ile Gly
                 55                  60                  65 ttg gga gag aag gcg ttt gag ttg gat aga aag agg aaa agg tat gtg      417
Leu Gly Glu Lys Ala Phe Glu Leu Asp Arg Lys Arg Lys Arg Tyr Val
             70                  75                  80 atg tat aac gtt gac gct ggg gct tat aag aaa tat caa gat cca ctt      465
Met Tyr Asn Val Asp Ala Gly Ala Tyr Lys Lys Tyr Gln Asp Pro Leu
         85                  90                  95 tac gtt agt ata ccc tta ttt ata tca gtg aaa gac ggc gtt gca act      513
Tyr Val Ser Ile Pro Leu Phe Ile Ser Val Lys Asp Gly Val Ala Thr
    100                 105                 110 ggt tac ttc ttc aac tca gct tct aaa gtg atc ttc gac gtg gga ctt      561
Gly Tyr Phe Phe Asn Ser Ala Ser Lys Val Ile Phe Asp Val Gly Leu
115                 120                 125                 130 gag gaa tac gat aaa gta att gtt aca att cca gag gac tca gta gag      609
Glu Glu Tyr Asp Lys Val Ile Val Thr Ile Pro Glu Asp Ser Val Glu
                135                 140                 145 ttt tac gtg att gaa ggg cca aga att gag gac gtt cta gag aaa tac      657
Phe Tyr Val Ile Glu Gly Pro Arg Ile Glu Asp Val Leu Glu Lys Tyr
            150                 155                 160 acg gag ctt acc gga aaa cct ttc cta cct ccc atg tgg gct ttc ggt      705
Thr Glu Leu Thr Gly Lys Pro Phe Leu Pro Pro Met Trp Ala Phe Gly
        165                 170                 175
```

-continued

```
tac atg ata tca cgc tac tct tac tac ccc cag gat aag gtt gtt gag      753
Tyr Met Ile Ser Arg Tyr Ser Tyr Tyr Pro Gln Asp Lys Val Val Glu
    180                 185                 190 tta gta gat ata atg caa aag gag ggt ttt aga gta gct gga gta ttc      801
Leu Val Asp Ile Met Gln Lys Glu Gly Phe Arg Val Ala Gly Val Phe
195                 200                 205                 210 tta gat ata cac tac atg gac tcc tat aag tta ttt aca tgg cat cct      849
Leu Asp Ile His Tyr Met Asp Ser Tyr Lys Leu Phe Thr Trp His Pro
                215                 220                 225 tat agg ttc cca gaa cct aaa aag cta att gac gaa tta cac aag aga      897
Tyr Arg Phe Pro Glu Pro Lys Lys Leu Ile Asp Glu Leu His Lys Arg
            230                 235                 240 aac gtt aag cta att aca ata gtt gac cac gga ata agg gtt gat cag      945
Asn Val Lys Leu Ile Thr Ile Val Asp His Gly Ile Arg Val Asp Gln
                245                 250                 255 aat tat tca cca ttt ctt tcc gga atg gga aaa ttc tgt gag att gaa      993
Asn Tyr Ser Pro Phe Leu Ser Gly Met Gly Lys Phe Cys Glu Ile Glu
260                 265                 270 agt ggt gaa cta ttc gta ggt aaa atg tgg cct ggt act act gtc tat     1041
Ser Gly Glu Leu Phe Val Gly Lys Met Trp Pro Gly Thr Thr Val Tyr
275                 280                 285                 290 cca gac ttc ttc agg gag gat act aga gaa tgg tgg gct ggg tta atc     1089
Pro Asp Phe Phe Arg Glu Asp Thr Arg Glu Trp Trp Ala Gly Leu Ile
                295                 300                 305 tcc gaa tgg ctt tca caa gga gtt gat ggt att tgg cta gac atg aat     1137
Ser Glu Trp Leu Ser Gln Gly Val Asp Gly Ile Trp Leu Asp Met Asn
            310                 315                 320 gaa cca act gac ttc tct agg gct att gag atc aga gac gtt tta tct     1185
Glu Pro Thr Asp Phe Ser Arg Ala Ile Glu Ile Arg Asp Val Leu Ser
                325                 330                 335 tcg tta ccc gta cag ttc aga gat gat aga ctt gtt acc act ttt cca     1233
Ser Leu Pro Val Gln Phe Arg Asp Asp Arg Leu Val Thr Thr Phe Pro
340                 345                 350 gat aac gta gtt cac tac ttg agg gga aag agg gtt aaa cac gaa aaa     1281
Asp Asn Val Val His Tyr Leu Arg Gly Lys Arg Val Lys His Glu Lys
355                 360                 365                 370 gtt aga aat gct tat cct tta tat gag gct atg gca acg ttt aag ggg     1329
Val Arg Asn Ala Tyr Pro Leu Tyr Glu Ala Met Ala Thr Phe Lys Gly
                375                 380                 385 ttt agg aca agc cat agg aat gaa ata ttt atc ttg agt aga gcc ggt     1377
Phe Arg Thr Ser His Arg Asn Glu Ile Phe Ile Leu Ser Arg Ala Gly
                390                 395                 400 tat gcc gga ata caa aga tac gca ttc atc tgg act ggt gat aat acc     1425
Tyr Ala Gly Ile Gln Arg Tyr Ala Phe Ile Trp Thr Gly Asp Asn Thr
            405                 410                 415 cct tca tgg gat gat ttg aag ctt caa cta caa ttg gtt ctc ggc tta     1473
Pro Ser Trp Asp Asp Leu Lys Leu Gln Leu Gln Leu Val Leu Gly Leu
420                 425                 430 tcg att tct ggt gta cca ttt gta ggt tgt gat ata ggt gga ttt caa     1521
Ser Ile Ser Gly Val Pro Phe Val Gly Cys Asp Ile Gly Gly Phe Gln
435                 440                 445                 450 ggc agg aac ttc gcg gaa att gac aac tct atg gat tta tta gtc aaa     1569
Gly Arg Asn Phe Ala Glu Ile Asp Asn Ser Met Asp Leu Leu Val Lys
                455                 460                 465 tat tat gct tta gcc ttg ttc ttc ccc ttc tat agg tca cac aag gca     1617
Tyr Tyr Ala Leu Ala Leu Phe Phe Pro Phe Tyr Arg Ser His Lys Ala
            470                 475                 480 act gat ggt ata gat acg gaa cca gtt ttc ctg cca gat tac tat aag     1665
Thr Asp Gly Ile Asp Thr Glu Pro Val Phe Leu Pro Asp Tyr Tyr Lys
485                 490                 495
```

```
gag aaa gta aag gaa atc gtg gag ttg agg tat aag ttc tta ccc tat      1713
Glu Lys Val Lys Glu Ile Val Glu Leu Arg Tyr Lys Phe Leu Pro Tyr
500                 505                 510 att tat tcc tta gct tta gag gct agt gag aag gga cat ccg gta att      1761
Ile Tyr Ser Leu Ala Leu Glu Ala Ser Glu Lys Gly His Pro Val Ile
515                 520                 525                 530 aga cct cta ttt tac gaa ttc cag gat gat gac gac atg tat aga ata      1809
Arg Pro Leu Phe Tyr Glu Phe Gln Asp Asp Asp Asp Met Tyr Arg Ile
            535                 540                 545 gaa gac gag tat atg gtt ggt aag tat ttg ctt tac gct cca att gta      1857
Glu Asp Glu Tyr Met Val Gly Lys Tyr Leu Leu Tyr Ala Pro Ile Val
        550                 555                 560 agt aaa gag gag agt agg tta gta aca tta cct aga ggt aag tgg tac      1905
Ser Lys Glu Glu Ser Arg Leu Val Thr Leu Pro Arg Gly Lys Trp Tyr
    565                 570                 575 aat tac tgg aat ggc gag ata ata aac ggt aag agt gtt gtt aag tct      1953
Asn Tyr Trp Asn Gly Glu Ile Ile Asn Gly Lys Ser Val Val Lys Ser
580                 585                 590 act cat gag ttg cca att tac ttg aga gaa gga tca ata atc ccg ttg      2001
Thr His Glu Leu Pro Ile Tyr Leu Arg Glu Gly Ser Ile Ile Pro Leu
595                 600                 605                 610 gag ggt gac gag tta ata gtt tac ggt gag acc tcg ttc aag cgt tac      2049
Glu Gly Asp Glu Leu Ile Val Tyr Gly Glu Thr Ser Phe Lys Arg Tyr
            615                 620                 625 gat aat gct gaa att acc tcc tca agt aat gaa att aag ttt tca agg      2097
Asp Asn Ala Glu Ile Thr Ser Ser Ser Asn Glu Ile Lys Phe Ser Arg
        630                 635                 640 gag att tat gta tct aag cta act atc aca tca gag aaa cca gtg agc      2145
Glu Ile Tyr Val Ser Lys Leu Thr Ile Thr Ser Glu Lys Pro Val Ser
    645                 650                 655 aag ata ata gtt gac gat agt aag gaa att caa gta gag aag aca atg      2193
Lys Ile Ile Val Asp Asp Ser Lys Glu Ile Gln Val Glu Lys Thr Met
660                 665                 670 caa aac act tac gtt gct aag att aat caa aaa att agg gga aag att      2241
Gln Asn Thr Tyr Val Ala Lys Ile Asn Gln Lys Ile Arg Gly Lys Ile
675                 680                 685                 690 aac cta gag tagttttttc acgtactcca aggacttaac                         2280
Asn Leu Glu <210> SEQ ID NO 2
<211> LENGTH: 693
<212> TYPE: PRT
<213> ORGANISM: Sulfolobus solfataricus

<400> SEQUENCE: 2

Met Gln Thr Ile Lys Ile Tyr Glu Asn Lys Gly Val Tyr Lys Val Val
1               5                   10                  15

Ile Gly Glu Pro Phe Pro Pro Ile Glu Phe Pro Leu Glu Gln Lys Ile
                20                  25                  30

Ser Ser Asn Lys Ser Leu Ser Glu Leu Gly Leu Thr Ile Val Gln Gln
            35                  40                  45

Gly Asn Lys Val Ile Val Glu Lys Ser Leu Asp Leu Lys Glu His Ile
        50                  55                  60

Ile Gly Leu Gly Glu Lys Ala Phe Glu Leu Asp Arg Lys Arg Lys Arg
65                  70                  75                  80

Tyr Val Met Tyr Asn Val Asp Ala Gly Ala Tyr Lys Lys Tyr Gln Asp
                85                  90                  95

Pro Leu Tyr Val Ser Ile Pro Leu Phe Ile Ser Val Lys Asp Gly Val
```

-continued

```
              100                 105                 110
Ala Thr Gly Tyr Phe Phe Asn Ser Ala Ser Lys Val Ile Phe Asp Val
            115                 120                 125
Gly Leu Glu Glu Tyr Asp Lys Val Ile Val Thr Ile Pro Glu Asp Ser
130                 135                 140
Val Glu Phe Tyr Val Ile Glu Gly Pro Arg Ile Glu Asp Val Leu Glu
145                 150                 155                 160
Lys Tyr Thr Glu Leu Thr Gly Lys Pro Phe Leu Pro Pro Met Trp Ala
                165                 170                 175
Phe Gly Tyr Met Ile Ser Arg Tyr Ser Tyr Pro Gln Asp Lys Val
                180                 185                 190
Val Glu Leu Val Asp Ile Met Gln Lys Glu Gly Phe Arg Val Ala Gly
            195                 200                 205
Val Phe Leu Asp Ile His Tyr Met Asp Ser Tyr Lys Leu Phe Thr Trp
210                 215                 220
His Pro Tyr Arg Phe Pro Glu Pro Lys Lys Leu Ile Asp Glu Leu His
225                 230                 235                 240
Lys Arg Asn Val Lys Leu Ile Thr Ile Val Asp His Gly Ile Arg Val
                245                 250                 255
Asp Gln Asn Tyr Ser Pro Phe Leu Ser Gly Met Gly Lys Phe Cys Glu
                260                 265                 270
Ile Glu Ser Gly Glu Leu Phe Val Gly Lys Met Trp Pro Gly Thr Thr
            275                 280                 285
Val Tyr Pro Asp Phe Phe Arg Glu Asp Thr Arg Glu Trp Trp Ala Gly
            290                 295                 300
Leu Ile Ser Glu Trp Leu Ser Gln Gly Val Asp Gly Ile Trp Leu Asp
305                 310                 315                 320
Met Asn Glu Pro Thr Asp Phe Ser Arg Ala Ile Glu Ile Arg Asp Val
                325                 330                 335
Leu Ser Ser Leu Pro Val Gln Phe Arg Asp Asp Arg Leu Val Thr Thr
                340                 345                 350
Phe Pro Asp Asn Val Val His Tyr Leu Arg Gly Lys Arg Val Lys His
                355                 360                 365
Glu Lys Val Arg Asn Ala Tyr Pro Leu Tyr Glu Ala Met Ala Thr Phe
            370                 375                 380
Lys Gly Phe Arg Thr Ser His Arg Asn Glu Ile Phe Ile Leu Ser Arg
385                 390                 395                 400
Ala Gly Tyr Ala Gly Ile Gln Arg Tyr Ala Phe Ile Trp Thr Gly Asp
                405                 410                 415
Asn Thr Pro Ser Trp Asp Asp Leu Lys Leu Gln Leu Gln Leu Val Leu
                420                 425                 430
Gly Leu Ser Ile Ser Gly Val Pro Phe Val Gly Cys Asp Ile Gly Gly
            435                 440                 445
Phe Gln Gly Arg Asn Phe Ala Glu Ile Asp Asn Ser Met Asp Leu Leu
            450                 455                 460
Val Lys Tyr Tyr Ala Leu Ala Leu Phe Phe Pro Phe Tyr Arg Ser His
465                 470                 475                 480
Lys Ala Thr Asp Gly Ile Asp Thr Glu Pro Val Phe Leu Pro Asp Tyr
                485                 490                 495
Tyr Lys Glu Lys Val Lys Glu Ile Val Glu Leu Arg Tyr Lys Phe Leu
                500                 505                 510
Pro Tyr Ile Tyr Ser Leu Ala Leu Glu Ala Ser Glu Lys Gly His Pro
            515                 520                 525
```

-continued

```
Val Ile Arg Pro Leu Phe Tyr Glu Phe Gln Asp Asp Asp Met Tyr
    530                 535                 540

Arg Ile Glu Asp Glu Tyr Met Val Gly Lys Tyr Leu Leu Tyr Ala Pro
545                 550                 555                 560

Ile Val Ser Lys Glu Glu Ser Arg Leu Val Thr Leu Pro Arg Gly Lys
                565                 570                 575

Trp Tyr Asn Tyr Trp Asn Gly Glu Ile Ile Asn Gly Lys Ser Val Val
                580                 585                 590

Lys Ser Thr His Glu Leu Pro Ile Tyr Leu Arg Glu Gly Ser Ile Ile
            595                 600                 605

Pro Leu Glu Gly Asp Glu Leu Ile Val Tyr Gly Glu Thr Ser Phe Lys
        610                 615                 620

Arg Tyr Asp Asn Ala Glu Ile Thr Ser Ser Ser Asn Glu Ile Lys Phe
625                 630                 635                 640

Ser Arg Glu Ile Tyr Val Ser Lys Leu Thr Ile Thr Ser Glu Lys Pro
                645                 650                 655

Val Ser Lys Ile Ile Val Asp Asp Ser Lys Glu Ile Gln Val Glu Lys
            660                 665                 670

Thr Met Gln Asn Thr Tyr Val Ala Lys Ile Asn Gln Lys Ile Arg Gly
        675                 680                 685

Lys Ile Asn Leu Glu
    690

<210> SEQ ID NO 3
<211> LENGTH: 19
<212> TYPE: PRT
<213> ORGANISM: Sulfolobus solfataricus

<400> SEQUENCE: 3

Met Gln Thr Ile Lys Ile Tyr Glu Asn Leu Gly Val Tyr Leu Trp Ile
1               5                   10                  15

Gly Glu Pro

<210> SEQ ID NO 4
<211> LENGTH: 10
<212> TYPE: PRT
<213> ORGANISM: Sulfolobus solfataricus

<400> SEQUENCE: 4

Val Gly Lys Tyr Leu Leu Tyr Ala Pro Ile
1               5                   10
```